United States Patent
Allen et al.

(10) Patent No.: US 6,756,218 B2
(45) Date of Patent: Jun. 29, 2004

(54) SUCROSE PHOSPHATE SYNTHASE

(75) Inventors: Stephen M. Allen, Wilmington, DE (US); Perry G. Caimi, Kennett Square, PA (US); Emil M. Orozco, Jr., West Grove, PA (US); Mitchell C. Tarczynski, West Des Moines, IA (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/918,909

(22) Filed: Jul. 31, 2001

(65) Prior Publication Data

US 2002/0090704 A1 Jul. 11, 2002

Related U.S. Application Data

(63) Continuation-in-part of application No. 09/697,367, filed on Oct. 26, 2000, now Pat. No. 6,323,015, which is a continuation of application No. PCT/US99/09865, filed on May 6, 1999.
(60) Provisional application No. 60/084,529, filed on May 7, 1998.

(51) Int. Cl.$^7$ .................. C12N 9/10; C12N 1/20; C12N 15/00; C12P 21/04; C07H 21/04
(52) U.S. Cl. ............... 435/193; 435/252.3; 435/320.1; 435/71.1; 536/23.2
(58) Field of Search .................. 435/193; 536/232

(56) References Cited

U.S. PATENT DOCUMENTS 5,665,892 A    9/1997   Van Assche et al.

FOREIGN PATENT DOCUMENTS

WO    WO 99/57285 A2    11/1999

OTHER PUBLICATIONS

Akira Komatsu et al., Mol Genet, vol. 252:346–351, 1996, Cloning and Molecular Analysis of CDNAs Encoding Three Sucrose Phosphate Synthase Isoforms from a Citrus Fruit.
Ann C. Worrell et al., The Plant Cell, vol. 3:1121–1130, 1991, Expression of a Maize Sucrose Phosphate Synthase in Tomato Alters Leaf Carbohydrate Partitioning.
National Center for Biotechnology Information General Identifier No.: 3915023, Dec. 15, 1998, Komatsu A., et. al., Cloning amd Molecular Analysis of CDNAS Encoding Three Sucrose Phosphate Synthase Isoforms from a Citrus Fruit.
National Center for Biotechnology Information General Identifier No.: 1854376, Feb. 13, 1999, Sugiharto, B. et. al., Differential Expression of Two Genes for Sucrose–Phosphate Synthase in Sugarcane: Molecular Cloning of the CDNAS and Comparative Analysis of Gene Expression.
National Center for Biotechnology Information General Identifier No.: 1854378, Feb. 13, 1999, Sugiharto, B. et. al., Differential Expression of Two Genes for Sucrose–Phosphate Synthase in Sugarcane: Molecular Cloning of the CDNAS and Comparative Analysis of Gene Expression.
National Center for Biotechnology Information General Identifier No.: 168626, Apr. 27, 1993, Worrell, A. C. et. al., Expression of a Maize Sucrose Phosphate in Tomato Alters Leaf Carbohydrate Partitioning.
National Center for Biotechnology Information General Identifier No.: 7433836, Jul. 16, 1999, Bevan, M. et. al.

*Primary Examiner*—Ponnathapu Achutamurthy
*Assistant Examiner*—Yong D. Pak

(57) ABSTRACT

This invention relates to an isolated nucleic acid fragment encoding a sucrose phosphate synthase. The invention also relates to the construction of a chimeric gene encoding all or a portion of the sucrose phosphate synthase, in sense or antisense orientation, wherein expression of the chimeric gene results in production of altered levels of the sucrose phosphate synthase in a transformed host cell.

7 Claims, 4 Drawing Sheets

FIGURE 1A

```
                                        *********************   *             *
SEQ ID NO:24    SARAETSRIRLQSNRQSRQGRSRGRRARRGEMAGNDWINSYLEAILDAGGAAGDLSAAAG
SEQ ID NO:29    ---------------------------MAGNDWINSYLEAILDVGPGLDD----------
                1                                                           60

****  **********  **********  **        **  *  ******
SEQ ID NO:24    SGDGRDGTAVEKRDKSSLMLRERGRFSPARYFVEEVISGFDETDLYKTWVRTSAMRSPQE
SEQ ID NO:29    ----------AKSSLLLRERGRFSPTRYFVEEVITGFDETDLHRSWVKAQATRSPQE
                61                                                          120

**********  **********  ***    *  *   *    **  ************
SEQ ID NO:24    RNTRLENMSWRIWNLARKKKQIEGEEASRLSKQRMEFEKAR-QYAADLSEDLSEGEKGET
SEQ ID NO:29    RNTRLENMCWRIWNLARQKKQLEGEAAQRMAKRRLERERGRREATADMSEDLSEGEKGDI
                121                                                         180

*   *   ***   *   **    *   **                ************
SEQ ID NO:24    NNEPSIHDESMRTRMPRIGSTDAIDTWANQHKDKKLYIVLISIHGLIRGENMELGRDSDT
SEQ ID NO:29    VSDVSAHGDSTRSRLPRISSVDAMETWISQQKGKKLYIVLISIHGLIRGENMELGRDSDT
                181                                                         240

***********  *******  **********  **********    *     **
SEQ ID NO:24    ---VKYVVELARALGSTPGVYRVDLLTRQISAPDVDWSYGEPTEMLSPISSENFGLELGE
SEQ ID NO:29    GGQVKYVVELARALGSMPGVYRVDLLTRQVSAPDVDWSYGEPTEMLTPRNSDDFMDDMGE
                241                                                         300

*******  *******  **  ***********  **********    ******  *
SEQ ID NO:24    SSGAYIVRIPFGPRDKYIPKEHLWPHIQEFVDGALVHIMQMSKVLGEQIGSGQPVWPVVI
SEQ ID NO:29    SSGAYIIRIPFGPKDKYIAKELLWPHIPEFVDGALNHIIRMSNVLGEQIGGGKPVWPVAI
                301                                                         360
```

FIGURE 1B

```
                 **********************  *  ***  ***********************
SEQ ID NO:24     HGHYADAGDSAALLSGALNVPMVFTGHSLGRDKLDQILKQGRQTRDEINATYKIMRRIEA
SEQ ID NO:29     HGHYADAGDSAALLSGALNVPMLFTGHSLGRDKLEQLLKQARLSRDEINATYKIMRRIEA
                                                                      420

***  ***  ****  **  ********  ** *  *  ****  ***  ****
SEQ ID NO:24     EELCLDTSEIIITSTRQEIEQQWGLYDGFDLTMARKLRARIRRGVSCFGRYMPRMIAIPP
SEQ ID NO:29     EELSLDASEIVITSTRQEIEEQWRLYDGFDPVLERKLRARIKRNVSCYGKFMPRMAIIPP
                                                                      480

****  ***  * ****  *  **********  ******  *************
SEQ ID NO:24     GMEFSHIAPHDVDLDSE-EGNGDGSGSPDPPIWADIMRFFSNPRKPMILALARPDPKKNI
SEQ ID NO:29     GMEFHHIVPQDGDMDGETEGNEDNPASPDPPIWSEIMRFFTNPRKPVILALARPDPKKNI
                                                                      540

******  **  **************  ******* ** ***  *************
SEQ ID NO:24     TTLVKAFGEHRELRNLANLTLIMGNRDVIDEMSSTNAAVLTSALKLIDKYDLYGQVAYPK
SEQ ID NO:29     TTLVKAFGECRPLRELANLTLIMGNRDGIDEMSSTSASVLLSVLKLIDKYDLYGQVAYPK
                                                                      600

******  **  ***********  ****  *  ***  ***  *************
SEQ ID NO:24     HHKQSEVPDIYRLAARTKGVFINCALVEPFGLTLIEAAAYGLPMVATRNGGPVDIHRVLD
SEQ ID NO:29     HHKQSDVPEIYRLAAKTKGVFINPAFIEPFGLTLIEAAAHGLPIVATKNGGPVDIHRVLD
                                                                      660

** ******  **  *******  **  *  *  ****  ********
SEQ ID NO:24     NGILVDPHNQEIAEALYKLVSDKHLWSQCRQNGLKNIHKFSWPEHCQNYLARVVTLKPR
SEQ ID NO:29     NGLLVDPHDQQSIADALLKLVAGKQLWARCRQNGLKNIHLFSWPEHCKTYLSRIAGCKPR
                                                                      720
```

FIGURE 1C

```
              **  *  *  *** ****** ******** *** ****                   ***
SEQ ID NO:24  HPRWQKNDVAAEISEADSPEDSLRDIHDISLNLKLSLDSEKSGSK------EGNSNAL
SEQ ID NO:29  HPQWQRTDDGGETSESDSPGDSLRDIQDISLNLKFSLDGEKSGASGNDDSLDSEGNVADR
                                                                      780

*     *  *                   *  ******** ** **
SEQ ID NO:24  RRHFEDAAQKLS--GVNDIKKDVPGEN------GKWSSLRRRKHIIVIAVDSVQDADFV
SEQ ID NO:29  KSRLENAVLAWSKGVLKDTRKSGSTDKVDQNTGAAKFPALRRRKHIFVISVDCDSTTGLL
                                                                      840

* ***  * *** **  ***     *           *  ***************
SEQ ID NO:24  QVIKNIFEASRNERSSGAVGFVLSTARAISELHTLLISGGIEASDFDAFICNSGSDLCYP
SEQ ID NO:29  DATKKICEAVEKERTEGSIGFILSTSMTISEIHSFLVSGHLSPSDFDAFICNSGSDLYYS
                                                                      900

*  **           ***           *** *          ***
SEQ ID NO:24  SSSSEDMLNPAELPFMIDLDYHSQIEYRWGGEGLRKTLIRWAA---EKNKESGQKIFIED
SEQ ID NO:29  T----LNSEDGPFVVDFYYHSHIEYRWGGEGLRKTLVRWASQVTDKKAESGEKVLTPA
                                                                      960

*  *  * **  ****    *  ****  *****  **  ** ***************
SEQ ID NO:24  EECSSTYCISFKVSNTAAAPPVKEIRRTMRIQALRCHVLYSHDGSKLNVIPVLASRSQAL
SEQ ID NO:29  EQLSTNYCYAFSVQKPGMTPPVKELRKVLRIQALRCHVIYCQNGSRVNVIPVLASRSQAL
                                                                      1020

****  *******     *  ***  ******************  *  *******
SEQ ID NO:24  RYLYIRWGVELSNITVIVGECGDTDYEGLLGGVHKTIILKGSFNTAPNQVHANRSYSSQD
SEQ ID NO:29  RYLYLRWGVELSKMVFVGESGDTDYEGLLGGVHKTVILKGICSSSSNQIHANRSYPLSD
                                                                      1080
```

FIGURE 1D

```
              *         *        *           *    *   *  **
SEQ ID NO:24  VVSFDKQGIASI-EGYGPDNLKSALRQFGILKD
SEQ ID NO:29  VMPIDSPNIVQTPEDCTTSDIRSSLEQLGLLKV
              1081                            1113
```

SUCROSE PHOSPHATE SYNTHASE

This application is a continuation-in-part of U.S. patent application Ser. No. 09/697,367, filed Oct. 26, 2000 now issued as U.S. Pat. No. 6,323,015, which is a continuation of PCT Application No. PCT/US99/09865, filed May 6, 1999, which claims the benefit of U.S. Provisional Application No. 60/084,529, filed May 7, 1998.

FIELD OF THE INVENTION

This invention is in the field of plant molecular biology. More specifically, this invention pertains to nucleic acid fragments encoding sucrose phosphate synthase in plants and seeds.

BACKGROUND OF THE INVENTION

In plants photosynthetically fixed carbon is ultimately converted into two main carbohydrate products, sucrose and starch. Sucrose is the form in which most fixed carbon is exported from the photosynthetic cell. Sucrose is then translocated to various parts of the plant which have a need for this sugar such as regions of active growth and developing seeds or tubers. Sucrose is synthesized in the cytoplasm of photosynthetic cells from the precursor dihydroxyacetone phosphate (DiHOAcP). In the last two steps of sucrose biosynthesis UDP-glucose is converted to sucrose by the successive action of sucrose phosphate synthase (SPS) (E.C. 2.4.1.14) and sucrose phosphatase. By modulating the level of SPS in plants it may be possible to control carbon partitioning in photosynthetic cells. Accordingly, the availability of nucleic acid sequences encoding all or a portion of a sucrose phosphate synthase protein would facilitate studies to better understand carbon partitioning in plants.

Worrell, A. C. et al. ((1991) *Plant Cell* 3:1121–1130) describe a maize cDNA that encodes a sucrose phosphate synthase as confirmed by the ability of the cloned sequence to direct sucrose phosphate synthesis in *E. coli*. Additional nucleic acid fragments encoding sucrose phosphate synthase have been isolated by other groups (e.g., U.S. Pat. No. 5,665,892; JP 2000262283).

SUMMARY OF THE INVENTION

The present invention concerns an isolated polynucleotide comprising: (a) a first nucleotide sequence encoding a first polypeptide comprising at least 400 amino acids, wherein the amino acid sequence of the first polypeptide and the amino acid sequence of SEQ ID NO:24 have at least 70%, 80%, 85%, 90%, or 95% identity based on the Clustal alignment method, (b) a second nucleotide sequence encoding a second polypeptide comprising at least 435 amino acids, wherein the amino acid sequence of the second polypeptide and the amino acid sequence of SEQ ID NO:28 have at least 70%, 80%, 85%, 90%, or 95% identity based on the Clustal alignment method, (c) a third nucleotide sequence encoding a third polypeptide comprising at least 150 amino acids, wherein the amino acid sequence of the third polypeptide and the amino acid sequence of SEQ ID NO:26 have at least 90% or 95% identity based on the Clustal alignment method, or (d) the complement of the first, second, or third nucleotide sequence, wherein the complement and the first, second, or third nucleotide sequence contain the same number of nucleotides and are 100% complementary. The first polypeptide preferably comprises the amino acid sequence of SEQ ID NO:24, the second polypeptide preferably comprises the amino acid sequence of SEQ ID NO:28, and the third polypeptide preferably comprises the amino acid sequence of SEQ ID NO:26. The first nucleotide sequence preferably comprises the nucleotide sequence of SEQ ID NO:23, the second nucleotide sequence preferably comprises the nucleotide sequence of SEQ ID NO:27, and the third nucleotide sequence preferably comprises the nucleotide sequence of SEQ ID NO:25. The first, second, and third polypeptides preferably are sucrose phosphate synthases.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, or 60 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a seventh embodiment, the present invention concerns an isolated polypeptide comprising: (a) a first amino acid sequence comprising at least 400 amino acids, wherein the first amino acid sequence and the amino acid sequence of SEQ ID NO:24 have at least 70%, 80%, 85%, 90%, or 95% identity based on the Clustal alignment method, (b) a second amino acid sequence comprising at least 435 amino acids, wherein the second amino acid sequence and the amino acid sequence of SEQ ID NO:28 have at least 70%, 80%, 85%, 90%, or 95% identity based on the Clustal alignment method, or (c) a third amino acid sequence comprising at least 150 amino acids, wherein the third amino acid sequence and the amino acid sequence of SEQ ID NO:26 have at least 90% or 95% identity based on the Clustal alignment method. The first amino acid sequence preferably comprises the amino acid sequence of SEQ ID NO:24, the second amino acid sequence preferably comprises the amino acid sequence of SEQ ID NO:28, and the third amino acid sequence preferably comprises the amino acid sequence of SEQ ID NO:26. The polypeptide preferably is a sucrose phosphate synthase.

In an eighth embodiment, the present invention relates to a virus, preferably a baculovirus, comprising any of the isolated polynucleotides of the present invention or any of the chimeric genes of the present invention.

In a ninth embodiment, the invention relates to a method of selecting an isolated polynucleotide that affects the level of expression of a sucrose phosphate synthase protein or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the sucrose phosphate synthase protein or enzyme activity in the host cell containing the isolated polynucleotide; and (d) comparing the level of the sucrose phosphate synthase protein or enzyme activity in the host cell containing the isolated polynucleotide with the level of the sucrose phosphate synthase protein or enzyme activity in the host cell that does not contain the isolated polynucleotide.

In a tenth embodiment, the invention concerns a method of obtaining a nucleic acid fragment encoding a substantial portion of a sucrose phosphate synthase protein, preferably a plant sucrose phosphate synthase protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NO:23, 25, and 27, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a sucrose phosphate synthase protein amino acid sequence.

In an eleventh embodiment, this invention relates to a method of obtaining a nucleic acid fragment encoding all or a substantial portion of the amino acid sequence encoding a sucrose phosphate synthase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the sucrose phosphate synthase polynucleotide in an amount sufficient to complement a null mutant to provide a positive selection means.

In a thirteenth embodiment, this invention relates to a method of altering the level of expression of a sucrose phosphate synthase protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the sucrose phosphate synthase protein in the transformed host cell.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A, 1B, 1C, and 1D depict the amino acid sequence alignment between the sucrose phosphate synthases encoded by the following: (a) nucleotide sequence of the insert in corn clone ceb5.pk0081.h10 (SEQ ID NO:24), and (b) nucleotide sequence from Citrus unshiu (NCBI GI No. 3915023; SEQ ID NO:29). Amino acids which are conserved between the two sequences are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs or PCR fragment sequence ("Contig*"), or sequences encoding the entire protein derived from an EST, an FIS, a contig, or an FIS and PCR fragment sequence ("CGS"). SEQ ID NOs:1–22 correspond to SEQ ID NOs:1–22, respectively, presented in U.S. patent application Ser. No. 09/697,367 filed on Oct. 26, 2000 and in WO 99/57285 which published Nov. 11, 1999. The sequence descriptions and Sequence Listing attached hereto comply with the rules governing nucleotide and/or amino acid sequence disclosures in patent applications as set forth in 37 C.F.R. §1.821–1.825.

TABLE 1

Sucrose Phosphate Synthase

| Plant | Clone Designation | Status | SEQ ID NO: (Nucleotide) | (Amino Acid) |
|---|---|---|---|---|
| Catalpa | ncs.pk0009.e3 | FIS | 1 | 2 |
| Barley | bsh1.pk0013.d3 | FIS | 3 | 4 |
| Corn | ceb5.pk0081.g10 | EST | 5 | 6 |
| Corn | Contig of p0130.cwtaf69r p0093.cssan39r p0094.cssst68r p0119.cmtoh35r p0127.cntag51r | Contig | 7 | 8 |
| Rice | Contig of rls12.pk0024.d8 rl0n.pk0002.e3 | Contig | 9 | 10 |
| Rice | rl0n.pk086.i23 | EST | 11 | 12 |
| Rice | rl0n.pk0056.d5 | EST | 13 | 14 |
| Soybean | sfl1.pk0048.a12(FIS) | CGS | 15 | 16 |
| Soybean | sfl1.pk0075.d7 | EST | 17 | 18 |
| Wheat | Contig of wr1.pk0028.h11(FIS) wr1.pk0112.a8 | Contig | 19 | 20 |
| Wheat | Contig of wkm1c.pk0002.g6 wr1.pk0046.c10 | Contig | 21 | 22 |
| Corn | ceb5.pk0081.h10(FIS) | CGS | 23 | 24 |
| Rice | rls12.pk0024.d8 | FIS | 25 | 26 |
| Wheat | wkm1c.pk0002.g6 | FIS | 27 | 28 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NO:23, 25, or 27, or the complement of such sequences.

The term "isolated" polynucleotide refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NO:23, 25, and 27, and the complement of such nucleotide sequences may be used in methods of selecting an isolated polynucleotide that affects the expression of a sucrose phosphate synthase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C.

for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250, 400, or 435 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising: (a) a first nucleotide sequence encoding a first polypeptide comprising at least 400 amino acids, wherein the amino acid sequence of the first polypeptide and the amino acid sequence of SEQ ID NO:24 have at least 70%, 80%, 85%, 90%, or 95% identity based on the Clustal alignment method, (b) a second nucleotide sequence encoding a second polypeptide comprising at least 435 amino acids, wherein the amino acid sequence of the second polypeptide and the amino acid sequence of SEQ ID NO:28 have at least 70%, 80%, 85%, 90%, or 95% identity based on the Clustal alignment method, (c) a third nucleotide sequence encoding a third polypeptide comprising at least 150 amino acids, wherein the amino acid sequence of the third polypeptide and the amino acid sequence of SEQ ID NO:26 have at least 90% or 95% identity based on the Clustal alignment method, or (d) the complement of the first, second, or third nucleotide sequence, wherein the complement and the first, second, or third nucleotide sequence contain the same number of nucleotides and are 100% complementary. The first polypeptide preferably comprises the amino acid sequence of SEQ ID NO:24, the second polypeptide preferably comprises the amino acid sequence of SEQ ID NO:28, and the third polypeptide preferably comprises the amino acid sequence of SEQ ID NO:26. The first nucleotide sequence preferably comprises the nucleotide sequence of SEQ ID NO:23, the second nucleotide sequence preferably comprises the nucleotide sequence of SEQ ID NO:27, and the third nucleotide sequence preferably comprises the nucleotide sequence of SEQ ID NO:25. The first, second, and third polypeptides preferably are sucrose phosphate synthases.

Nucleic acid fragments encoding at least a portion of several sucrose phosphate synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other sucrose phosphate synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NO:23, 25, and 27, and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a sucrose phosphate synthase polypeptide, preferably a substantial portion of a plant sucrose phosphate synthase polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NO:23, 25, and 27, and the complement of such nucleotide sequences; and amplifying a nucleic acid fragment (preferably a cDNA inserted in a cloning vector) using the oligonucleotide primer. The amplified nucleic acid fragment preferably will encode a portion of a sucrose phosphate synthase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of sucrose and sucrose biosynthetic activity in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an isolated polypeptide comprising: (a) a first amino acid sequence comprising at least 400 amino acids, wherein the first amino acid sequence and the amino acid sequence of SEQ ID NO:24 have at least 70%, 80%, 85%, 90%, or 95% identity based on the Clustal alignment method, (b) a second amino acid sequence comprising at least 435 amino acids, wherein the second amino acid sequence and the amino acid sequence of SEQ ID NO:28 have at least 70%, 80%, 85%, 90%, or 95% identity based on the Clustal alignment method, or (c) a third amino acid sequence comprising at least 150 amino acids, wherein the third amino acid sequence and the amino acid sequence of SEQ ID NO:26 have at least 90% or 95% identity based on the Clustal alignment method. The first amino acid sequence preferably comprises the amino acid sequence of SEQ ID NO:24, the second amino acid sequence preferably comprises the amino acid sequence of SEQ ID NO:28, and the third amino acid sequence preferably comprises the amino acid sequence of SEQ ID NO:26. The polypeptide preferably is a sucrose phosphate synthase.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sucrose phosphate synthase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide.

Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various catalpa (*Catalpa speciosa*), barley (*Hordeum vulgare*), corn (*Zea mays*), rice (*Oryza sativa*), soybean (*Glycine max*), and wheat (*Triticum aestivum*) tissues were prepared. The characteristics of the libraries are described below. Corn developmental stages (e.g., V-12) are explained in the publication "How a corn plant develops" from the Iowa State University Coop. Ext. Service Special Report No. 48 reprinted June 1993.

TABLE 2 cDNA Libraries from Barley, Corn, Catalpa, Rice, Soybean and Wheat

| Library | Tissue | Clone |
| --- | --- | --- |
| bsh1 | Barley Sheath, Developing Seedling | bsh1.pk0013.d3 |
| ceb5 | Corn Embryo 30 Days After Pollination | ceb5.pk0081.g10 |
|  |  | ceb5.pk0081.h10 |
| ncs | *Catalpa speciosa* Developing Seed | ncs.pk0009.e3 |
| p0093 | Corn Stalk And Shank | p0093.cssan39r |
| p0094 | Corn Leaf Collar For The Ear Leaf And The Next Next Leaf Above And Below | p0094.cssst68r |
| p0119 | Corn Night Harvested Ear Shoot/ W Husk: V-12 Stage | p0119.cmtoh35r |
| p0127 | Corn Nucellus Tissue, 5 Days After Silking | p0127.cntag51r |
| p0130 | Corn Wild-Type Internode Tissue | p0130.cwtaf69r |
| rl0n | Rice 15 Day Old Leaf* | rl0n.pk0002.e3 |
|  |  | rl0n.pk0056.d5 |
|  |  | rl0n.pk086.i23 |

TABLE 2-continued cDNA Libraries from Barley, Corn, Catalpa, Rice, Soybean and Wheat

| Library | Tissue | Clone |
| --- | --- | --- |
| rls12 | Susceptible Rice Leaf 15 Days After Germination, 12 Hours After Infection Of *Magnaporthe grisea* Strain 4360-R-67 (AVR2-YAMO) | rls12.pk0024.d8 |
| sfl1 | Soybean Immature Flower | sfl1.pk0048.a12 |
|  |  | sfl1.pk0075.d7 |
| wkm1c | Wheat Kernel Malted 55 Hours at 22° C. | wkm1c.pk0002.g6 |
| wr1 | Wheat Root, 7 Day Old Seedling, Light Grown | wr1.pk0028.h11 |
|  |  | wr1.pk0046.c10 |
|  |  | wr1.pk0112.a8 |

*This library was normalized essentially as described in U.S. Pat. No. 5,482,845 cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding sucrose phosphate synthase were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Sucrose Phosphate Synthase

The BLASTX search using the EST sequences from several clones revealed similarity of the proteins encoded by the cDNAs to sucrose phosphate synthase from different organisms. The BLAST results for each of these ESTs are shown in Table 3:

TABLE 3

BLAST Results for Clones Encoding Polypeptides Homologous to Sucrose Phosphate Synthase (SPS)

| Clone | Protein | Organism | GenBank Accession No. | Blast pLog score |
|---|---|---|---|---|
| bsh1.pk0013.d3 | SPS | Saccharum officinarum | AB001338 | 68.00 |
| ceb5.pk0080.g10 | SPS | Beta vulgaris | X81975 | 20.40 |
| ncs.pk0009.e3 | SPS | Solanum tuberosum | X73477 | 46.52 |
| rls12.pk0024.d8 | SPS | Saceharum officinarum | AB001338 | 64.7 |
| sfl1.pk0048.a12 | SPS | Actinidia deliciosa | U85449 | 54.52 |
| sfl1.pk0075.d7 | SPS | Craterostigma plantagineum | Y11795 | 52.05 |
| sfl1.pk0080.c11 | SPS | Vicia faba | Z56278 | 30.70 |
| wkm1c.pk0002.g6 | SPS | Oryza sativa | U33175 | 30.00 |
| wr1.pk0028.h11 | SPS | Saccharum officinarum | AB001338 | 60.70 |

The sequence of the entire cDNA insert in clone ncs.pk0009.e3 was determined and is shown in SEQ ID NO:1; the deduced amino acid sequence of this cDNA is shown in SEQ ID NO:2. The sequence of the entire cDNA insert in clone bsh1.pk0013.d3 was determined and is shown in SEQ ID NO:3; the deduced amino acid sequence of this cDNA is shown in SEQ ID NO:4. Additional sequence of the cDNA insert in clone ceb5.pk0081.g10 was determined and is shown in SEQ ID NO:5; the deduced amino acid sequence of this portion of the cDNA insert is shown in SEQ ID:6. TBLASTN analysis of the proprietary plant EST database indicated that additional corn clones besides ceb5.pk0081.g10 encoded sucrose phosphate synthase. A contig was assembled using the sequence from a portion of the cDNA insert in clones p0130.cwtaf69r, p0093.cssan39r, p0094.cssst68r, p0119.cmtoh35r and p0127.cntag51r. The sequence of this contig is shown in SEQ ID NO:7; the deduced amino acid sequence of this contig is shown in SEQ ID NO:8. TBLASTN analysis of the proprietary plant EST database indicated that additional rice clones besides rls12.pk0024.d8 encoded sucrose phosphate synthase. These are clones rl0n.pk0002.e3, rl0n.pk086.i23 and rl0n.pk0056.d5. A contig was assembled using the sequence from a portion of the cDNA insert in clones rls12.pk0024.d8 and rl0n.pk0002.e3. The sequence of this contig is shown in SEQ ID NO:9; the deduced amino acid sequence of this contig is shown in SEQ ID NO:10. The sequence of a portion of the cDNA insert in clone rl0n.pk086.i23 is shown in SEQ ID NO: 11; the deduced amino acid sequence of this portion of the cDNA insert is shown in SEQ ID NO:12. The sequence of a portion of the cDNA insert in clone rl0n.pk0056.d5 is shown in SEQ ID NO:13; the deduced amino acid sequence of this portion of the cDNA insert is shown in SEQ ID NO:14. TBLASTN analysis of the proprietary plant EST database indicated that additional soybean clones besides sfl1.pk0048.a12 and sfl1.pk0075.d7 encoded sucrose phosphate synthase. These are clones sfl1.pk0080.c11, sdp3c.pk018.k22, sdp2c.pk021.o13 and sgc6c.pk001.14.The sequence of the entire cDNA insert in clone sfl1.pk0048.a12 was determined and is shown in SEQ ID NO:15; the deduced amino acid sequence of this cDNA is shown in SEQ ID NO:16. The nucleotide sequence in SEQ ID NO:15 includes the sequences from clones sfl1.pk0080.c11 (which was previously listed separately), sdp3c.pk018.k22, sdp2c.pk021.o13 and sgc6c.pk001.14. The sequence of a portion of the cDNA insert in clone sfl1.pk0075.d7 is shown in SEQ ID NO:17; the deduced amino acid sequence of this portion of the cDNA insert is shown in SEQ ID NO:18. TBLASTN analysis of the proprietary plant EST database indicated that additional wheat clones besides wkm1c.pk0002.g6 and wr1.pk0028.h11 encoded sucrose phosphate synthase. These are clones wr1.pk0112.a8 and wr1.pk0046.c10. A contig was assembled using the sequence from the entire cDNA insert in clone wr1.pk0028.h11 and a portion of the cDNA insert in clone wr1.pk0112.a8. The sequence of this contig is shown in SEQ ID NO:19; the deduced amino acid sequence of this contig is shown in SEQ ID NO:20. A contig was assembled using the sequence from a portion of the cDNA insert in clones wkm1c.pk0002.g6 and wr1.pk0046.c10. The sequence of this contig is shown in SEQ ID NO:21; the deduced amino acid sequence of this contig is shown in SEQ ID NO:22.

The BLASTX search using the nucleotide sequences mentioned above revealed similarity of the proteins encoded by the cDNAs to sucrose phosphate synthase from different species. The BLASTX results for each of these sequences are shown in Table 4:

TABLE 4

BLAST Results for Clones Encoding Polypeptides Homologous to Sucrose Phosphate Synthase

| Clone | Organism | BLAST Results NCBI General Identifier No. | pLog Score |
|---|---|---|---|
| ncs.pk0009.e3 | Craterostigma plantagineum | 3915021 | 105 |
| bsh1.pk0013.d3 | Saccharum officinarum | 1854378 | 90 |
| ceb5.pk0081.g10 | Musa acuminata | 3237273 | 27.3 |
| Contig of p0130.cwtaf69r p0093.cssan39r p0094.cssst68r p0119.cmtoh35r p0127.cntag5ir | Craterostigma plantagineum | 3915021 | >250 |
| Contig of rls12.pk0024.d8 rl0n.pk0002.e3 | Saccharum officinarum | 1854378 | 131 |
| rl0n.pk086.i23 | Saccharum officinarum | 1854378 | 58.7 |
| rl0n.pk0056.d5 | Saccharum officinarum | 1854378 | 68.4 |
| sfl1.pk0048.a12 | Citrus unshiu | 3915023 | >250 |
| sfl1.pk0075.d7 | Craterostigma plantagineum | 3915022 | 56.7 |
| Contig of wr1.pk0112.a8 wr1.pk0028.h11 | Saccharum officinarum | 1854378 | >250 |
| Contig of wkm1c.pk0002.g6 wr1.k0046.c10 | Zea mays | 401114 | 84.5 |

The *Citrus unshiu* sequence is 75.1% identical to the amino acid sequence presented in SEQ ID NO:2 and 83.3% identical to the amino acid sequence presented in SEQ ID NO:16.

The BLASTX search also revealed that of two sugarcane sucrose phosphate synthase amino acid sequences (NCBI General Identifier Nos. 1854376 and 1854378), one of these sequences (NCBI Gene Identifier No. 1854376) displayed considerably more homology to the corn sucrose phosphate synthase amino acid sequence disclosed in U.S. Pat. No. 5,665,892 (NCBI Gene Identifier No. 168626). Accordingly, the nucleic acid fragments described in Table 4 may therefore be classified as encoding polypeptides similar to the corn SPS disclosed in U.S. Pat. No. 5,665,892 or similar to the sugar cane SPS set forth in NCBI Gene Identifier No. 1854378. Using this criterion, the amino acid sequences set forth in SEQ ID NO:2, SEQ ID NO:18 and SEQ ID NO:22 are similar to the SPS sequence disclosed in U.S. Pat. No. 5,665,892, whereas amino acid sequences set forth in SEQ ID NO:4, SEQ ID NO:6, SEQ ID NO:8, SEQ ID NO:10, SEQ ID NO:12, SEQ ID NO:14, SEQ ID NO:16 and SEQ ID NO:20 encode a different SPS that is similar to the sugar cane SPS set forth in NCBI Gene Identifier No. 1854378.

The sequence disclosed in U.S. Pat. No. 5,665,892 is 67.7% similar to the amino acid sequence presented in SEQ ID NO:8, clearly indicating that the corn amino acid sequence presented in SEQ ID NO:8 is distinct from the sucrose phosphate synthase amino acid sequence disclosed in U.S. Pat. No. 5,665,892.

Sequence alignments and percent similarity calculations were performed using the Megalign program of the LASERGENE bioinformatics computing suite (DNASTAR Inc., Madison, Wis.). Multiple alignment of the sequences and percent similarity calculations were performed using the Clustal method of alignment (Higgins, D. G. and Sharp, P. M. (1989) *CABIOS.* 5:151–153) using the default parameters (GAP PENALTY=10, GAP LENGTH PENALTY=10).

BLAST scores and probabilities indicate that the instant nucleic acid fragments encode entire soybean and substantial portions of barley, corn, Catalpa, rice, soybean and wheat sucrose phosphate synthase enzymes that are distinguishable from other sucrose phosphate sequences known in the art. These sequences also represent the first barley, Catalpa, rice, soybean and wheat sequences encoding the instant sucrose phosphate synthase protein.

The BLASTX search using the EST sequences from clones listed in Table 5 revealed similarity of the polypeptides encoded by the cDNAs to sucrose phosphate synthase from *Saccharum officinarum* (NCBI GenBank Identifier (GI) No. 1854378), *Arabidopsis thaliana* (NCBI GI No. 7433836), and *Citrus unshiu* (NCBI GI No. 3915023). Shown in Table 5 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 5

BLAST Results for Sequences Encoding Polypeptides Homologous to Sucrose Phosphate Synthase

| | | BLAST Results | |
|---|---|---|---|
| Clone | Status | NCBI GI No. | pLog Score |
| ceb5.pk0081.h10(FIS) | CGS | 3915023 | >180.00 |
| rls12.pk0024.d8 | FIS | 1854378 | >180.00 |
| wkm1c.pk0002.g6 | FIS | 7433836 | 104.00 |

Isolation and initial characterization of clones rls12.pk0024.d8 and wkm1c.pk0002.g6 have been previously described in U.S. patent application Ser. No. 09/697,367 filed on Oct. 26, 2000 and in WO 99/57285 which published Nov. 11, 1999.

FIGS. 1A, 1B, 1C, and 1D present an alignment of the amino acid sequence set forth in SEQ ID NO:24 and the *Citrus unshiu* sequence (NCBI GI No.3915023; SEQ ID NO:29). The data in Table 6 represents a calculation of the percent identity of the amino acid sequence set forth in SEQ ID NO:24 and the *Citrus unshiu* sequence (NCBI GI No. 3915023; SEQ ID NO:29).

TABLE 6

Percent Identity of Amino Acid Sequences Deduced From the Nucleotide Sequences of cDNA Clones Encoding Polypeptides Homologous to Sucrose Phosphate Synthase

| SEQ ID NO. | Percent Identity to NCBI GI No. 3915023; SEQ ID NO:29 |
|---|---|
| 2 | 66.0 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode a substantial portion of a sucrose phosphate synthase.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature (London)* 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having sucrose phosphate synthase activity, wherein the polypeptide has an amino acid sequence of SEQ ID NO:24, or
   (b) a complement of the nucleotide sequence of (a), wherein the complement and the nucleotide sequence consist of the same number of nucleotides and are 100% complementary.

2. The polynucleotide of claim 1 wherein the nucleotide sequence comprises SEQ ID NO:23.

3. A vector comprising the polynucleotide of claim 1.

4. A recombinant DNA construct comprising the polynucleotide of claim 1 operably linked to at least one regulatory sequence.

5. A method for transforming a cell, comprising transforming a cell with the recombinant DNA construct of claim 4.

6. A host cell comprising the recombinant DNA construct of claim 4.

7. A method for production of a polypeptide having sucrose phosphate synthase activity comprising the steps of cultivating the cell of claim 6 under conditions that allow for the synthesis of the polypeptide and isolating the polypeptide from the cultivated cells, from culture medium, or from both the cultivated cells and the culture medium.

* * * * *

UNITED STATES PATENT AND TRADEMARK OFFICE
CERTIFICATE OF CORRECTION

PATENT NO. : 6,756,218 B2
DATED : June 29, 2004
INVENTOR(S) : Allen Stephen M. et al.

It is certified that error appears in the above-identified patent and that said Letters Patent is hereby corrected as shown below:

Title page,
Item [75], Inventors, delete "J. Antoni Rafalski, Wilmington, DE (US)".

Columns 28 and 29,
Sequence Listing, delete the complete Sequence Listing starting at the bottom of columns 28 and 29 through the top of columns 89 and 90 of the last page of the patent and replace with the complete substitute Sequence Listing filed on December 24, 2002.

Signed and Sealed this

Twenty-eighth Day of September, 2004

JON W. DUDAS
*Director of the United States Patent and Trademark Office*

SEQUENCE LISTING

<160> NUMBER OF SEQ ID NOS: 29

<210> SEQ ID NO 1
<211> LENGTH: 2236
<212> TYPE: DNA
<213> ORGANISM: Catalpa speciosa

<400> SEQUENCE: 1

```
gcacgagaga tagaggagca gtggcgtttg tatgatggtt ttgatccaat actagagcgt      60
aaactacgtg ctaggattag gcgtaatgtc agctgttacg gaaggttcat gcctcgcatg     120
gttgtaattc cacctgggat ggaattccat cacatagttc cacatgatgg agacatggat     180
actgaagctg aagcaaacga agatggaaag tctccagaaa cacctatttg ggcagaggta     240
atgcgtttct tttcaaatcc aaggaagcct atgattcttg cacttgccag gccagatcca     300
aagaaaaacc tcactacctt ggtcaaagca tttggggaat gtcgaccact aagggagctt     360
gctaatctta ccttgataat gggtaataga gataatattg atgaaatgtc gggaaccaat     420
gcttcagttc ttctatcaat ccttaagatg attgacaagt atgatctcta tggtcaagtg     480
gcatatccta aacatcacaa gcaacatgat gttcctgaaa tttaccgtct agcagcaaag     540
accaagggtg ttttcataaa tccagctttt atcgagcctt ttgggcttac tctcattgag     600
```

```
gctacagcat atggtttgcc aattgttgcg acgaaaaatg gtggccctgt tgatatacac    660
aaggttctgg acaatggtct ccttgttgat ccccacaatc agcagtccat tgctgatgct    720
cttttgaagc tggttgcgga taagcatctc tgggcgaaat gtagagcaaa tggattaaaa    780
aatattcacc tttttcatg gccagaacat tgtagaactt atctctccaa aatagcaagt     840
tgcaaaccaa ggcaacctcg ttggttgaga atgacgatg atgatgaaaa ttcagaatca     900
gattcaccaa gtgactcctt gagggatata caagatatat ctttgaacct caagttctcc    960
tttgaaggag ataagaatga gaatcgggaa aatatcggtg gttccttaga ctctgaagac   1020
cgaaagagta agctagaaaa tgctgtattg acgtggtcta agggtgtggt gaaaggtgca   1080
caaaaatctg ggtctactga taaaggagac cagaatccta tgctggtaa gttcccagca    1140 ttgaggagga gaaaacacat ttttgtgatt gctgtggata atgatgcaag tgctggtctt   1200
tctgaaagtg ttaaaaagat ctttgaggct gtggagaagg aaaaaagtga aggctcagtt   1260
ggatttatat tagctacgtc ctttaacatc acacaaacat gttctttct ggtttcagaa    1320 ggattgaacc ccacagaatt tgacgcattt atatgcaata gtggcggtga tctttattac   1380
tcatctattc attcagaaaa taatccgttt gtggtggact tgtattatca ttcacatatt   1440
gaataccgat ggggagggga agggttgagg aagactttag tgcgttgggc agcttctata   1500
actgataaga ctggagaaaa ggaagaacac attattgttg aagatgaaga acttcggcc    1560 gactactgct attcttttaa agttcaaaag cctggagtgg ttcccccagt aaaggaactt   1620
agaaagttga tgagaattca ggcactacga tgtcatgtca tccattgtca aaatggaagt   1680
aagatcaacg taattccagt ttcggcttct cgttcccaag cactcaggta tctgtatctt   1740
cgctggggta tggacttgtc gaaagtagtt gttttttgtcg gggaaagcgg agacagcgac   1800
tatgaaggtt tgcttggcgg cgttaacaag tctgtagtgc tgggcggagt ttgcaccaat   1860
gcgagcagcc aactccatgc caaccgaagc tatcctctca cagatgtcgt atattatgac   1920
agtcctaata ttaccagaac ctctgaagga tttagcagct cggatctccg agcctcgctg   1980
gcggaggtag gtgttctcaa gacctaaaat ttttgcttac cgccttgtac acatgttcag   2040
cttaaaataa taagcatcaa cttatggatt gcttcctgtt tataattcgg ctgcataatg   2100
atgtgttata ttttctcaat aaacctttga gatgagacca ttttttcttt gttgcccttt   2160
ctggaggaat tgaaactgta atgggacatg ttcaattttc tcctttgtca tacaagcaaa   2220 aaaaaaaaa aaatca                                                    2236
```

<210> SEQ ID NO 2
<211> LENGTH: 668
<212> TYPE: PRT
<213> ORGANISM: Catalpa speciosa

<400> SEQUENCE: 2

```
Ala Arg Glu Ile Glu Gln Trp Arg Leu Tyr Asp Gly Phe Asp Pro
1               5                  10                 15

Ile Leu Glu Arg Lys Leu Arg Ala Arg Ile Arg Arg Asn Val Ser Cys
            20                  25                  30

Tyr Gly Arg Phe Met Pro Arg Met Val Val Ile Pro Pro Gly Met Glu
        35                  40                  45

Phe His His Ile Val Pro His Asp Gly Asp Met Asp Thr Glu Ala Glu
    50                  55                  60

Ala Asn Glu Asp Gly Lys Ser Pro Glu Thr Pro Ile Trp Ala Glu Val
65                  70                  75                  80
```

```
Met Arg Phe Phe Ser Asn Pro Arg Lys Pro Met Ile Leu Ala Leu Ala
                85                  90                  95

Arg Pro Asp Pro Lys Lys Asn Leu Thr Thr Leu Val Lys Ala Phe Gly
            100                 105                 110

Glu Cys Arg Pro Leu Arg Glu Leu Ala Asn Leu Thr Leu Ile Met Gly
            115                 120                 125

Asn Arg Asp Asn Ile Asp Glu Met Ser Gly Thr Asn Ala Ser Val Leu
            130                 135                 140

Leu Ser Ile Leu Lys Met Ile Asp Lys Tyr Asp Leu Tyr Gly Gln Val
145                 150                 155                 160

Ala Tyr Pro Lys His His Lys Gln His Asp Val Pro Glu Ile Tyr Arg
            165                 170                 175

Leu Ala Ala Lys Thr Lys Gly Val Phe Ile Asn Pro Ala Phe Ile Glu
            180                 185                 190

Pro Phe Gly Leu Thr Leu Ile Glu Ala Thr Ala Tyr Gly Leu Pro Ile
            195                 200                 205

Val Ala Thr Lys Asn Gly Gly Pro Val Asp Ile His Lys Val Leu Asp
    210                 215                 220

Asn Gly Leu Leu Val Asp Pro His Asn Gln Gln Ser Ile Ala Asp Ala
225                 230                 235                 240

Leu Leu Lys Leu Val Ala Asp Lys His Leu Trp Ala Lys Cys Arg Ala
            245                 250                 255

Asn Gly Leu Lys Asn Ile His Leu Phe Ser Trp Pro Glu His Cys Arg
            260                 265                 270

Thr Tyr Leu Ser Lys Ile Ala Ser Cys Lys Pro Arg Gln Pro Arg Trp
            275                 280                 285

Leu Arg Asn Asp Asp Asp Glu Asn Ser Glu Ser Asp Ser Pro Ser
    290                 295                 300

Asp Ser Leu Arg Asp Ile Gln Asp Ile Ser Leu Asn Leu Lys Phe Ser
305                 310                 315                 320

Phe Glu Gly Asp Lys Asn Glu Asn Arg Glu Asn Ile Gly Gly Ser Leu
            325                 330                 335

Asp Ser Glu Asp Arg Lys Ser Lys Leu Glu Asn Ala Val Leu Thr Trp
            340                 345                 350

Ser Lys Gly Val Val Lys Gly Ala Gln Lys Ser Gly Ser Thr Asp Lys
            355                 360                 365

Gly Asp Gln Asn Pro Asn Ala Gly Lys Phe Pro Ala Leu Arg Arg Arg
    370                 375                 380

Lys His Ile Phe Val Ile Ala Val Asp Asn Asp Ala Ser Ala Gly Leu
385                 390                 395                 400

Ser Glu Ser Val Lys Lys Ile Phe Glu Ala Val Glu Lys Glu Lys Ser
            405                 410                 415

Glu Gly Ser Val Gly Phe Ile Leu Ala Thr Ser Phe Asn Ile Thr Gln
            420                 425                 430

Thr Cys Ser Phe Leu Val Ser Glu Gly Leu Asn Pro Thr Glu Phe Asp
            435                 440                 445

Ala Phe Ile Cys Asn Ser Gly Gly Asp Leu Tyr Tyr Ser Ser Ile His
    450                 455                 460

Ser Glu Asn Asn Pro Phe Val Val Asp Leu Tyr Tyr His Ser His Ile
465                 470                 475                 480

Glu Tyr Arg Trp Gly Gly Glu Gly Leu Arg Lys Thr Leu Val Arg Trp
            485                 490                 495
```

```
Ala Ala Ser Ile Thr Asp Lys Thr Gly Glu Lys Glu His Ile Ile
            500                 505                 510
Val Glu Asp Glu Glu Thr Ser Ala Asp Tyr Cys Tyr Ser Phe Lys Val
            515                 520                 525
Gln Lys Pro Gly Val Val Pro Pro Val Lys Glu Leu Arg Lys Leu Met
        530                 535                 540
Arg Ile Gln Ala Leu Arg Cys His Val Ile His Cys Gln Asn Gly Ser
545                 550                 555                 560
Lys Ile Asn Val Ile Pro Val Ser Ala Ser Arg Ser Gln Ala Leu Arg
                565                 570                 575
Tyr Leu Tyr Leu Arg Trp Gly Met Asp Leu Ser Lys Val Val Val Phe
            580                 585                 590
Val Gly Glu Ser Gly Asp Ser Asp Tyr Glu Gly Leu Leu Gly Gly Val
            595                 600                 605
Asn Lys Ser Val Val Leu Gly Gly Val Cys Thr Asn Ala Ser Ser Gln
        610                 615                 620
Leu His Ala Asn Arg Ser Tyr Pro Leu Thr Asp Val Val Tyr Tyr Asp
625                 630                 635                 640
Ser Pro Asn Ile Thr Arg Thr Ser Glu Gly Phe Ser Ser Ser Asp Leu
                645                 650                 655
Arg Ala Ser Leu Ala Glu Val Gly Val Leu Lys Thr
            660                 665

<210> SEQ ID NO 3
<211> LENGTH: 863
<212> TYPE: DNA
<213> ORGANISM: Hordeum vulgare

<400> SEQUENCE: 3
gcacgagctt cctcgatagt agaaagaagg ggaagaactg aaaaacaagt tatctttgaa      60
gacgcagaac actcctcaac atcttgcctt gcgtttagag tggtcaatcc aaattattta     120
cctcctttga aggagctgca gaagttgatg agaatccagt cactacgctg tcatgctctt     180
tataaccaca gtgctaccag gctatctgta attccaattc atgcatcacg ctcccaggct     240
ctaaggtacc tgtctgttcg ttggggcata gagttgcgaa acgtcgtgat tcttgtcggt     300
gaaagcggcg attcagatta cgaagagctg tttggaggcc ttcacaagac gatcgtcctg     360
aagggcgagt tcaacacacc cgcaaacaga atccacacgg tcaggcggta cccgctgcaa     420
gacgtcatcg cgctcgattg ctcgaacatc atcggggtcg agggctgcag caccgacgac     480
ctgaccccta ctctgaagac gctcggcata ccgacgaagt gacacataga catatatttt     540
tgcctttttt tctttatacg atgagaggac cgaacaatat acgaatatag caaatatata     600
ctatcgtttc catgctggat ggaaataccg attttgcctg caagccgtgt tgtggccgtc     660
accttgagct gtgaataacg acattacgat catgttggcc ctgtcatgtg aaattcggc     720 gatgaagaac gaatccagag caggagggaa atctgttgaa cgcttcaaaa gtgttgttaa     780
gagaacattt gaaggaagca ttgatccaaa aaaaaaaaaa aaaaaaaata aactcgaggg     840
gggcccgtac acaaggtacg ccc                                             863

<210> SEQ ID NO 4
<211> LENGTH: 171
<212> TYPE: PRT
<213> ORGANISM: Hordeum vulgare

<400> SEQUENCE: 4
```

```
Ala Ser Ser Ile Val Glu Arg Gly Arg Thr Glu Lys Gln Val Ile
 1               5                  10                  15

Phe Glu Asp Ala Glu His Ser Thr Ser Cys Leu Ala Phe Arg Val
                 20                  25                  30

Val Asn Pro Asn Tyr Leu Pro Leu Lys Glu Leu Gln Lys Leu Met
             35                  40                  45

Arg Ile Gln Ser Leu Arg Cys His Ala Leu Tyr Asn His Ser Ala Thr
 50                  55                  60

Arg Leu Ser Val Ile Pro Ile His Ala Ser Arg Ser Gln Ala Leu Arg
 65                  70                  75                  80

Tyr Leu Ser Val Arg Trp Gly Ile Glu Leu Arg Asn Val Val Ile Leu
                 85                  90                  95

Val Gly Glu Ser Gly Asp Ser Asp Tyr Glu Glu Leu Phe Gly Gly Leu
                100                 105                 110

His Lys Thr Ile Val Leu Lys Gly Glu Phe Asn Thr Pro Ala Asn Arg
            115                 120                 125

Ile His Thr Val Arg Arg Tyr Pro Leu Gln Asp Val Ile Ala Leu Asp
        130                 135                 140

Cys Ser Asn Ile Ile Gly Val Glu Gly Cys Ser Thr Asp Asp Leu Thr
145                 150                 155                 160

Pro Thr Leu Lys Thr Leu Gly Ile Pro Thr Lys
                165                 170

<210> SEQ ID NO 5
<211> LENGTH: 511
<212> TYPE: DNA
<213> ORGANISM: Zea mays
<220> FEATURE:
<221> NAME/KEY: unsure
<222> LOCATION: (169)
<221> NAME/KEY: unsure
<222> LOCATION: (333)
<221> NAME/KEY: unsure
<222> LOCATION: (379)
<221> NAME/KEY: unsure
<222> LOCATION: (404)
<221> NAME/KEY: unsure
<222> LOCATION: (406)
<221> NAME/KEY: unsure
<222> LOCATION: (409)
<221> NAME/KEY: unsure
<222> LOCATION: (431)
<221> NAME/KEY: unsure
<222> LOCATION: (491)
<221> NAME/KEY: unsure
<222> LOCATION: (494)
<221> NAME/KEY: unsure
<222> LOCATION: (496)
<221> NAME/KEY: unsure
<222> LOCATION: (506)

<400> SEQUENCE: 5
cagaaacctc caggatccga ctccaatcga atcgccaaag cagacagggg cgctcgcggg      60
ggcgccgagc tcgacggggc gagatggccg ggaacgactg gatcaacagc tacctggagg     120
ctattctgga cgctggcggg gccgcggag atctctcggc agccgcagna gcggggacgg     180
ccgcgacggg acggccgtgg agaagcggga taagtcgtcg ctgatgctcc gagagcgcgg     240
ccggttcagc cccgcgcgat acttcgtcga ggaggtcatc tccggcttcg acgagaccga     300
cctctacaag acctgggtcc gcactcggct atnaggagtc cccaggaacg aaacacgcgg     360
ctggagacat gtcgtggang attggaactc ccaggaagaa gaanantana gagagaagct     420
acatttctaa naacgcatga tttagaaact cgtaatatct ctattgtcta aactattgat     480
```

```
gagaaaggaa ncantntatc atcatnatga g                                   511
```

```
<210> SEQ ID NO 6
<211> LENGTH: 18
<212> TYPE: PRT
<213> ORGANISM: Zea mays

<400> SEQUENCE: 6

Met Ala Gly Asn Asp Trp Ile Asn Ser Tyr Leu Glu Ala Ile Leu Asp
 1               5                  10                  15

Ala Gly

<210> SEQ ID NO 7
<211> LENGTH: 1611
<212> TYPE: DNA
<213> ORGANISM: Zea mays
<220> FEATURE:
<221> NAME/KEY: unsure
<222> LOCATION: (14)
<221> NAME/KEY: unsure
<222> LOCATION: (1424)
<221> NAME/KEY: unsure
<222> LOCATION: (1469)
<221> NAME/KEY: unsure
<222> LOCATION: (1505)
<221> NAME/KEY: unsure
<222> LOCATION: (1515)
<221> NAME/KEY: unsure
<222> LOCATION: (1560)

<400> SEQUENCE: 7
gggagtatac agantggatc tactaacaag gcagatttct gcacctgatg ttgattggag     60
ttatgggaa cctactgaga tgctcagtcc aataagttca gaaaactttg ggcttgagct    120
gggcgaaagc agtggtgcct atattgtccg gataccattc ggaccaagag acaaatatat   180
ccctaaagag catctatggc ctcacatcca ggaatttgtt gatggcgcac ttgtccatat   240
catgcagatg tccaaggtcc ttggagaaca aattggtagt gggcaaccag tatggcctgt   300
tgttatacat ggacactatg ctgatgctgg tgattctgct gctttactgt ctggggcact   360
caatgtaccc atggtattca ctggtcattc tcttggcaga gataagttgg accagatttt   420
gaagcaaggg cgtcaaacca gggatgaaat aaatgcaacc tataagataa tgcgtcgaat   480
tgaggccgag gaactttgcc ttgatacatc tgaaatcata attacaagta ccaggcaaga   540
aatagaacag caatggggat tatatgatgg ttttgatcta actatggccc ggaaactcag   600
agcaaggaat aaggcgtggt gtgagctgct ttggtcgtta catgccccgt atgattgcaa   660
tccctcctgg catggagttt agtcatatag caccacatga tgttgacctc gacagtgagg   720
aaggaaatgg agatggctca ggttcaccag atccacctat ttgggctgat ataatgcgct   780
tcttctcaaa cccccggaag ccaatgattc ttgctcttgc tcgtccggat ccgaagaaga   840
atatcactac tctagtcaaa gcatttggtg aacatcgtga actgagaaat ttagcaaatc   900
ttacactgat caatggggaa accgtgatgg tcattgatga aatgtcaagc acaaatgcag   960
ctgttttgac ttcagcactc aagttaattg ataaatatga tctatatgga caagtggcat  1020
acccccaagca ccataagcaa tctgaagttc ctgatattta tcgtttarct gcgagaacaa  1080
aaggagtttt tatcaattgg gcattgggtt gaaccaattg gactcaactt gattgaggct  1140
gctgcatatg gtctacccat ggttgccaac ccgaaatggt ggggcctgtg gacaatacat  1200
ccgggttctt ggataatggg aaattcctgg gttgacccccc acaatcaaaa tgaaatagct  1260
```

-continued

```
gaggcacttt ataagcttgt gtcagataag cacttgtggt cacaatgtcg ccagaatggt      1320
ctgaaaaaca tccataaatt ttcatggcct gaacattgcc agaactattt ggcacgtgta      1380
gtcactctca agcctagaca tccccgctgg caaaagaatg atgntgcagc tgaaatatct      1440
gaagcagatt cacccgagga ctctttgang gatattcatg acatatcact taacttaaag     1500
ctttncttgg acagnggaaa atcaggcagc aaagaaggga attcaaatgc ttttgagaan     1560 gcatttgag gatgcagcgc aaaagttgca aggtggtaat gacatcaaaa a              1611
```

<210> SEQ ID NO 8
<211> LENGTH: 365
<212> TYPE: PRT
<213> ORGANISM: Zea mays
<220> FEATURE:
<221> NAME/KEY: UNSURE
<222> LOCATION: (5)
<221> NAME/KEY: UNSURE
<222> LOCATION: (205)
<221> NAME/KEY: UNSURE
<222> LOCATION: (356)

<400> SEQUENCE: 8

Gly Val Tyr Arg Xaa Asp Leu Leu Thr Arg Gln Ile Ser Ala Pro Asp
 1               5                  10                  15

Val Asp Trp Ser Tyr Gly Glu Pro Thr Glu Met Leu Ser Pro Ile Ser
            20                  25                  30

Ser Glu Asn Phe Gly Leu Glu Leu Gly Glu Ser Ser Gly Ala Tyr Ile
        35                  40                  45

Val Arg Ile Pro Phe Gly Pro Arg Asp Lys Tyr Ile Pro Lys Glu His
    50                  55                  60

Leu Trp Pro His Ile Gln Glu Phe Val Asp Gly Ala Leu Val His Ile
65                  70                  75                  80

Met Gln Met Ser Lys Val Leu Gly Glu Gln Ile Gly Ser Gly Gln Pro
                85                  90                  95

Val Trp Pro Val Val Ile His Gly His Tyr Ala Asp Ala Gly Asp Ser
            100                 105                 110

Ala Ala Leu Leu Ser Gly Ala Leu Asn Val Pro Met Val Phe Thr Gly
        115                 120                 125

His Ser Leu Gly Arg Asp Lys Leu Asp Gln Ile Leu Lys Gln Gly Arg
    130                 135                 140

Gln Thr Arg Asp Glu Ile Asn Ala Thr Tyr Lys Ile Met Arg Arg Ile
145                 150                 155                 160

Glu Ala Glu Glu Leu Cys Leu Asp Thr Ser Glu Ile Ile Ile Thr Ser
                165                 170                 175

Thr Arg Gln Glu Ile Glu Gln Gln Trp Gly Leu Tyr Asp Gly Phe Asp
            180                 185                 190

Leu Thr Met Ala Arg Lys Leu Arg Ala Arg Asn Lys Xaa Gly Val Ser
        195                 200                 205

Cys Phe Gly Arg Tyr Met Pro Arg Met Ile Ala Ile Pro Pro Gly Met
    210                 215                 220

Glu Phe Ser His Ile Ala Pro His Asp Val Asp Leu Asp Ser Glu Glu
225                 230                 235                 240

Gly Asn Gly Asp Gly Ser Gly Ser Pro Asp Pro Ile Trp Ala Asp
                245                 250                 255

Ile Met Arg Phe Phe Ser Asn Pro Arg Lys Pro Met Ile Leu Ala Leu
            260                 265                 270

Ala Arg Pro Asp Pro Lys Lys Asn Ile Thr Thr Leu Val Lys Ala Phe

```
                275                 280                 285
Gly Glu His Arg Glu Leu Arg Asn Leu Ala Asn Leu Thr Leu Ile Asn
            290                 295                 300
Gly Glu Thr Val Met Val Ile Asp Glu Met Ser Ser Thr Asn Ala Ala
305                 310                 315                 320
Val Leu Thr Ser Ala Leu Lys Leu Ile Asp Lys Tyr Asp Leu Tyr Gly
                325                 330                 335
Gln Val Ala Tyr Pro Lys His His Lys Gln Ser Glu Val Pro Asp Ile
            340                 345                 350
Tyr Arg Leu Xaa Ala Arg Thr Lys Gly Val Phe Ile Asn
            355                 360                 365

<210> SEQ ID NO 9
<211> LENGTH: 661
<212> TYPE: DNA
<213> ORGANISM: Oryza sativa

<400> SEQUENCE: 9
gcacgaggaa gtgaagagct tctcaagcaa gggagacaga caagggagca aataaacatg      60
acatacaaaa taatgtgtag aattgaggca gaggagttgg ctcttgatgc atctgaaata     120
gttatagcaa gcactaggca agagataaga gagcaatgga atttgtatga cggttttgag     180
gtcatacttg caaggaaact ccgtgcaaga gtcaagcgtg gtgctaactg ctatggtcgc     240
tatatgcctc gtatggttat cattccccca ggtgttgaat ttggccatat gattcatgac     300
ttcgatatag gatggtgaag aagaaaatcc atgtccagcc tctgaggacc cacccatttg     360
gtctcagata atgcgcttct ttacaaatcc taggaagcct atgattctgg ctgttgctcg     420
tccatatcct gaaagaata ttacatcact tgtaaaggca tttggtgaat gtcgccctct     480
aagggagcta gcaaatctga cactgataat gggtaaccgt gaggccattt ctaagatgaa     540
caacatgagt gctgctgtct tgacctcagt gcttacattg attgatgaat atgacttgta     600
tggtcaagtg gcttatccca agcatcataa gcactctgaa gttccagctt ctcaagcaag     660
g                                                                    661

<210> SEQ ID NO 10
<211> LENGTH: 210
<212> TYPE: PRT
<213> ORGANISM: Oryza sativa
<220> FEATURE:
<221> NAME/KEY: UNSURE
<222> LOCATION: (100)

<400> SEQUENCE: 10

Glu Glu Leu Leu Lys Gln Gly Arg Gln Thr Arg Glu Gln Ile Asn Met
1               5                   10                  15
Thr Tyr Lys Ile Met Cys Arg Ile Glu Ala Glu Glu Leu Ala Leu Asp
            20                  25                  30
Ala Ser Glu Ile Val Ile Ala Ser Thr Arg Gln Glu Ile Glu Glu Gln
        35                  40                  45
Trp Asn Leu Tyr Asp Gly Phe Glu Val Ile Leu Ala Arg Lys Leu Arg
    50                  55                  60
Ala Arg Val Lys Arg Gly Ala Asn Cys Tyr Gly Arg Tyr Met Pro Arg
65                  70                  75                  80
Met Val Ile Ile Pro Pro Gly Val Glu Phe Gly His Met Ile His Asp
                85                  90                  95
Phe Asp Ile Xaa Asp Gly Glu Glu Glu Asn Pro Cys Pro Ala Ser Glu
```

```
            100                 105                 110
Asp Pro Pro Ile Trp Ser Gln Ile Met Arg Phe Phe Thr Asn Pro Arg
        115                 120                 125

Lys Pro Met Ile Leu Ala Val Ala Arg Pro Tyr Pro Glu Lys Asn Ile
130                 135                 140

Thr Ser Leu Val Lys Ala Phe Gly Glu Cys Arg Pro Leu Arg Glu Leu
145                 150                 155                 160

Ala Asn Leu Thr Leu Ile Met Gly Asn Arg Glu Ala Ile Ser Lys Met
                165                 170                 175

Asn Asn Met Ser Ala Ala Val Leu Thr Ser Val Leu Thr Leu Ile Asp
            180                 185                 190

Glu Tyr Asp Leu Tyr Gly Gln Val Ala Tyr Pro Lys His His Lys His
        195                 200                 205

Ser Glu
    210

<210> SEQ ID NO 11
<211> LENGTH: 546
<212> TYPE: DNA
<213> ORGANISM: Oryza sativa
<220> FEATURE:
<221> NAME/KEY: unsure
<222> LOCATION: (451)
<221> NAME/KEY: unsure
<222> LOCATION: (484)
<221> NAME/KEY: unsure
<222> LOCATION: (523)
<221> NAME/KEY: unsure
<222> LOCATION: (539)

<400> SEQUENCE: 11
cttacacctt gttgatccac atgatcagaa tgccattgca gatgcactgt ataagcttct      60
ttctgacaaa caactttggt cgagatgtag agagaatggg ctaaaaaata ttccaccagtt    120 ctcatggcct gaacattgca agaattactt gtcaaggata ttgacacttg gtccgagatc    180
acctgctatt ggtggcaaac aggaacagaa ggcacccata tcaggaagga agcatatcat    240
tgttatatct gtagactctg ttaacaagga agatctagtc cggataatca gaaacactat    300
tgaagtcaca cgcacagaaa aaatgtctgg ttcaactggg ttttgtgctg tcaacttcac    360
ttacaatatc aggagatacg cctcgctggc taagtgtctg caaggcatgt ttgcctactg    420 gtttttttgga tgccttcaac ctgcaataag nggggaagtt aatatcctaa taacccttg    480 gtantcccgg aagatacgc caaagcaagt tcccaaggtt acncccctggc aataagatnt    540 aaaatt                                                              546

<210> SEQ ID NO 12
<211> LENGTH: 112
<212> TYPE: PRT
<213> ORGANISM: Oryza sativa

<400> SEQUENCE: 12

Leu Val Asp Pro His Asp Gln Asn Ala Ile Ala Asp Ala Leu Tyr Lys
1               5                   10                  15

Leu Leu Ser Asp Lys Gln Leu Trp Ser Arg Cys Arg Glu Asn Gly Leu
            20                  25                  30

Lys Asn Ile His Gln Phe Ser Trp Pro Glu His Cys Lys Asn Tyr Leu
        35                  40                  45

Ser Arg Ile Leu Thr Leu Gly Pro Arg Ser Pro Ala Ile Gly Gly Lys
    50                  55                  60
```

```
Gln Glu Gln Lys Ala Pro Ile Ser Gly Arg Lys His Ile Ile Val Ile
 65                  70                  75                  80

Ser Val Asp Ser Val Asn Lys Glu Asp Leu Val Arg Ile Ile Arg Asn
                 85                  90                  95

Thr Ile Glu Val Thr Arg Thr Glu Lys Met Ser Gly Ser Thr Gly Phe
            100                 105                 110
```

<210> SEQ ID NO 13
<211> LENGTH: 601
<212> TYPE: DNA
<213> ORGANISM: Oryza sativa
<220> FEATURE:
<221> NAME/KEY: unsure
<222> LOCATION: (308)
<221> NAME/KEY: unsure
<222> LOCATION: (393)
<221> NAME/KEY: unsure
<222> LOCATION: (463)
<221> NAME/KEY: unsure
<222> LOCATION: (467)
<221> NAME/KEY: unsure
<222> LOCATION: (484)
<221> NAME/KEY: unsure
<222> LOCATION: (498)
<221> NAME/KEY: unsure
<222> LOCATION: (504)
<221> NAME/KEY: unsure
<222> LOCATION: (506)
<221> NAME/KEY: unsure
<222> LOCATION: (582)
<221> NAME/KEY: unsure
<222> LOCATION: (587)
<221> NAME/KEY: unsure
<222> LOCATION: (593)
<221> NAME/KEY: unsure
<222> LOCATION: (600)

<400> SEQUENCE: 13

```
cttacatgta agctcgtgcc gaattcggca cgagcttaca ctttgtattc gggagatacg    60
ccaagcagtt cccaggttac tcctgcaata gatcaaaatc accaagcaca tattgagtat   120
cgatggggag gagaaggcct aagaaagtat ctagtgaaat gggctacttc agtggtagaa   180
agaaagggaa gaatcgaaag acaaattatt tttgaagacc ctgaacactc ttcaacctat   240
tgtcttgcat ttagagtggt caatccaaat catctacccc cttttaaagga gttgaggaaa   300
ttgatganaa tccaatcact ccgttgcaat gccttgtata accacagtgc caccagactc   360
tctgtagttc ccattcacgc atcacgttcc agncactaag tacttgtgta tacctgggga   420
atagactgca aatgttgcat cctgttggta aagtggcatc ggntatnaga cgctagtggc   480
tcanagacgt catctaangg cgantnactc ccgcaacaat catacgtcag gaatacgtac   540
agagctccct gacactaata cattgcatga ggtaatcaat anagagnact cgncaattgn   600
g                                                                  601
```

<210> SEQ ID NO 14
<211> LENGTH: 118
<212> TYPE: PRT
<213> ORGANISM: Oryza sativa
<220> FEATURE:
<221> NAME/KEY: UNSURE
<222> LOCATION: (91)

<400> SEQUENCE: 14

```
Tyr Thr Leu Tyr Ser Gly Asp Thr Pro Ser Ser Gln Val Thr Pro
 1               5                  10                  15
```

```
Ala Ile Asp Gln Asn His Gln Ala His Ile Glu Tyr Arg Trp Gly Gly
         20                  25                  30
Glu Gly Leu Arg Lys Tyr Leu Val Lys Trp Ala Thr Ser Val Val Glu
     35                  40                  45
Arg Lys Gly Arg Ile Glu Arg Gln Ile Ile Phe Glu Asp Pro Glu His
 50                  55                  60
Ser Ser Thr Tyr Cys Leu Ala Phe Arg Val Val Asn Pro Asn His Leu
 65                  70                  75                  80
Pro Pro Leu Lys Glu Leu Arg Lys Leu Met Xaa Ile Gln Ser Leu Arg
                 85                  90                  95
Cys Asn Ala Leu Tyr Asn His Ser Ala Thr Arg Leu Ser Val Val Pro
             100                 105                 110
Ile His Ala Ser Arg Ser
             115

<210> SEQ ID NO 15
<211> LENGTH: 3524
<212> TYPE: DNA
<213> ORGANISM: Glycine max

<400> SEQUENCE: 15
```

| | | | | | |
|---|---|---|---|---|---|
| gcacgaggaa | agtatttccg | atgacataaa | cttgtttgaa | ttctccttgg | cagcagcaag | 60 |
| aagcagagta | taaatggcag | gaaacgattg | gctgaacagc | taccttgaag | ctatacttga | 120 |
| cgtgggtcct | ggcctggacg | atgccaagtc | ctctcttctt | ctccgagaga | gaggcaggtt | 180 |
| cagccctact | cgctacttcg | tccaagaggt | tattggcttc | gatgagaccg | atctctatcg | 240 |
| ctcttgggtt | cgggcttcct | ccaccaggag | tcctcaggag | aggaacacca | ggctcgagaa | 300 |
| catgtgctgg | cggatttgga | acctcgctcg | ccaaaagaag | cagctggaga | gtgagactgc | 360 |
| gctgagagtc | aacaagcgtc | gtttggagcg | cgagcggggt | cgcagggaag | ccaccgctga | 420 |
| tatgtcggag | gacttgtcgg | aaggagagaa | gggcgatccc | ttgagtgact | tgtccgctca | 480 |
| cggcggcgtc | ggcgacttca | accgatccag | gttgcccaga | atcagttccg | ctgatgccat | 540 |
| ggagacttgg | gccaacagtc | agaaagggaa | gaagctctac | attgtgctca | tcagcattca | 600 |
| tggcctaata | cgaggcgaga | atatggagct | gggacgtgat | tctgacacgg | tggtcaggt | 660 |
| taagtacgtt | gtggaacttg | caagggcatt | gggatcaatg | ccaggagttt | atcgggttga | 720 |
| tttgctaact | agacaagtgt | cggcgccaga | tgtagattgg | agttatgggg | agccgacgga | 780 |
| aatgttgtct | ccaagagaca | cagatgattt | tggagatgac | actggagaaa | gcagtggttc | 840 |
| ttatatcgtt | cgtattccct | tggtccaag | agataaatat | attccaaaag | aacttctctg | 900 |
| gccttacatt | cctgaatttg | ttgatggagc | gcttaaccac | attatacaga | tgtccaagtc | 960 |
| tcttggggaa | cagattggca | gtgggcatgc | tgtctggcct | gttgccatcc | acggacatta | 1020 |
| tgcagatgca | ggtgactctg | ctgctcttct | gtctggcgca | ttaaatgttc | caatgctttt | 1080 |
| tactggccac | tcacttggcc | gagataagtt | ggaacaactt | ttaaagcaag | gtagactatc | 1140 |
| aaaggatgaa | ataaacacaa | cttacaagat | tatgcgtagg | attgaagctg | aggaattggc | 1200 |
| ccttgatggt | tctgaaatag | tcatcacaag | cactagacag | gaaatagaag | aacaatggcg | 1260 |
| cttgtatgat | ggttttgatc | ctgtattgga | gcgtaaacta | cgagcaagga | tcaggcgtaa | 1320 |
| tgtgagctgc | tatgggagat | tcatgcctcg | catggcgaca | attccacctg | gtatggagtt | 1380 |
| ccatcatatt | gttccacacg | atggtgtata | agaaggtgaa | ccagaaggaa | atttggatca | 1440 |
| tcctgccccc | caagatccac | ctatttggtc | tgagataatg | cgcttcttta | ccaaccctcg | 1500 |

-continued

```
caagcctatg atacttgctc tcgctagacc agaccctaaa aagaacatca caactttggt    1560
aaaagcattt ggagaatgcc gtcctcttca agagcttgcc aaccttacat taattatggg    1620
taaccgagat ggaattgatg agatgtcaag cacaaatgct tctgttcttc tctcggtact    1680
taagttgatt gacaagtatg atctgtatgg gcaagtggca tatcctaaac atcacaaaca    1740
atatgatgtt cctgacatat atcgcctagc agcaaagaca aagggtgttt tcattaatcc    1800
agctttcatt gagccatttg gtcttacctt aattgaggca gctgctcatg gtttgccaat    1860
tgttgatact aaaaatggag gtcctgttga tattcatagg gtacttgaca atggtctgct    1920
cgtagatccc catgatcagc agtctattgc tgatgctctt ttgaagcttg ttagcaacaa    1980
acaactttgg gcaaaatgta gacagaatgg gttaaagaat attcatttat tttcatggcc    2040
cgagcactgt aagacttacc tttctaaaat agccacttgc aagccaaggc atccacaatg    2100
gcagcgaagt gaggatggag gtgaaagttc agaatcagat tcaccaggtg attccttgag    2160
agatttacag gacttgtctc taaatctgaa gttttcatta gatggagaga agagtgaggg    2220
tagtggaaat gacaattctt tgaattctga tggaaatgct gctgatagag ggcaaaatt    2280 agagaatgct gttttgtcat ggtcaaaggg catctctaag gacacacgca ggggtggggc    2340
tacagaaaaa tccgatcaga atccaaatgc tggtaaattt cctccattaa ggagaagaaa    2400
acatctgttt gtcattgctg tggattgtga taccacttca agccttcttg aaactattaa    2460
agccatcttt gagtctgctg gaaaggatag ggcagagagc attgtaggtt tcatattgtc    2520
aacatcatta acaatatcag agatacagtc atttctaatc tcaggtggct tgagtcccat    2580
tgattttgat gcttatattt gcaatagtgg cagtgatcta tactatccat ccctcaatcc    2640
cggagatcgc ccatttgtgg ttgacttgta ttaccactca cacattgaat accgttgggg    2700
tggagaaggg ttgaggaaga ctttagtgcg atgggctgat tcaatcactg ataagaaggg    2760
tgataatgac gaacaaattg tgagtcctgc tgaacagctt tctactgact actgttatgc    2820
tttcaaagtg cgaaagccag gaatggctcc ccctgtgaag gagcttcgca agttattacg    2880
gatccaagct ctgcgttgcc atccgatata ttgtcaaaat gggacaagac tgaatgtcat    2940
tccagtgctg gcatctcgtt cccaagccct cagatacctt tatgttcgat ggggttttga    3000
actgtcaaag atggtggtgt tcgttggaga atgcggtgac acagattacg aaggacttct    3060
tggtggccta cacaaaagtg tcatactgaa gggagtggga agcagtgcaa tcagtcaact    3120
ccataataac agaagctacc ctctttcaga tgtcacgcca ttggacagcc caacatcgt    3180 cgaggcaact gagggagta gcggtgctga tatccaggct ttgatcgaaa aagtgggata    3240
tctcaatgga tgaaaaaatt tgaaagtcat ttctagttat atgcctctta gtgtgtgtct    3300
gctatgaaac ctacttctga gcaagcagat atctgaattt tatccacaat gttcataaag    3360 ctttttttcct cctctcttct ctgtaacttc tatatcattc tcttcctcac aaacttcccc    3420
atgaaacata tttcctcttg tttccccact tatctccttg ttggttctgt atctacatat    3480 tacatttta atgaaggcca cttctcaaaa aaaaaaaaa aaaa                       3524
```

<210> SEQ ID NO 16
<211> LENGTH: 1059
<212> TYPE: PRT
<213> ORGANISM: Glycine max

<400> SEQUENCE: 16

```
Met Ala Gly Asn Asp Trp Leu Asn Ser Tyr Leu Glu Ala Ile Leu Asp
 1               5                  10                  15
```

-continued

```
Val Gly Pro Gly Leu Asp Asp Ala Lys Ser Ser Leu Leu Arg Glu
            20                  25                  30

Arg Gly Arg Phe Ser Pro Thr Arg Tyr Phe Val Gln Glu Val Ile Gly
        35                  40                  45

Phe Asp Glu Thr Asp Leu Tyr Arg Ser Trp Val Arg Ala Ser Ser Thr
    50                  55                  60

Arg Ser Pro Gln Glu Arg Asn Thr Arg Leu Glu Asn Met Cys Trp Arg
65                  70                  75                  80

Ile Trp Asn Leu Ala Arg Gln Lys Lys Gln Leu Glu Ser Glu Thr Ala
                85                  90                  95

Leu Arg Val Asn Lys Arg Leu Glu Arg Glu Arg Gly Arg Glu
            100                 105                 110

Ala Thr Ala Asp Met Ser Glu Asp Leu Ser Glu Gly Glu Lys Gly Asp
        115                 120                 125

Pro Leu Ser Asp Leu Ser Ala His Gly Gly Val Gly Asp Phe Asn Arg
    130                 135                 140

Ser Arg Leu Pro Arg Ile Ser Ser Ala Asp Ala Met Glu Thr Trp Ala
145                 150                 155                 160

Asn Ser Gln Lys Gly Lys Lys Leu Tyr Ile Val Leu Ile Ser Ile His
                165                 170                 175

Gly Leu Ile Arg Gly Glu Asn Met Glu Leu Gly Arg Asp Ser Asp Thr
            180                 185                 190

Gly Gly Gln Val Lys Tyr Val Glu Leu Ala Arg Ala Leu Gly Ser
        195                 200                 205

Met Pro Gly Val Tyr Arg Val Asp Leu Leu Thr Arg Gln Val Ser Ala
    210                 215                 220

Pro Asp Val Asp Trp Ser Tyr Gly Glu Pro Thr Glu Met Leu Ser Pro
225                 230                 235                 240

Arg Asp Thr Asp Asp Phe Gly Asp Asp Thr Gly Glu Ser Ser Gly Ser
                245                 250                 255

Tyr Ile Val Arg Ile Pro Phe Gly Pro Arg Asp Lys Tyr Ile Pro Lys
            260                 265                 270

Glu Leu Leu Trp Pro Tyr Ile Pro Glu Phe Val Asp Gly Ala Leu Asn
        275                 280                 285

His Ile Ile Gln Met Ser Lys Ser Leu Gly Glu Gln Ile Gly Ser Gly
    290                 295                 300

His Ala Val Trp Pro Val Ala Ile His Gly His Tyr Ala Asp Ala Gly
305                 310                 315                 320

Asp Ser Ala Ala Leu Leu Ser Gly Ala Leu Asn Val Pro Met Leu Phe
                325                 330                 335

Thr Gly His Ser Leu Gly Arg Asp Lys Leu Glu Gln Leu Leu Lys Gln
            340                 345                 350

Gly Arg Leu Ser Lys Asp Glu Ile Asn Thr Thr Tyr Lys Ile Met Arg
        355                 360                 365

Arg Ile Glu Ala Glu Leu Ala Leu Asp Gly Ser Glu Ile Val Ile
    370                 375                 380

Thr Ser Thr Arg Gln Glu Ile Glu Glu Gln Trp Arg Leu Tyr Asp Gly
385                 390                 395                 400

Phe Asp Pro Val Leu Glu Arg Lys Leu Arg Ala Arg Ile Arg Arg Asn
                405                 410                 415

Val Ser Cys Tyr Gly Arg Phe Met Pro Arg Met Ala Thr Ile Pro Pro
            420                 425                 430

Gly Met Glu Phe His His Ile Val Pro His Asp Gly Asp Ile Glu Gly
```

-continued

```
                435                 440                 445
Glu Pro Glu Gly Asn Leu Asp His Pro Ala Pro Gln Asp Pro Pro Ile
        450                 455                 460
Trp Ser Glu Ile Met Arg Phe Phe Thr Asn Pro Arg Lys Pro Met Ile
465                 470                 475                 480
Leu Ala Leu Ala Arg Pro Asp Pro Lys Lys Asn Ile Thr Thr Leu Val
                485                 490                 495
Lys Ala Phe Gly Glu Cys Arg Pro Leu Gln Glu Leu Ala Asn Leu Thr
            500                 505                 510
Leu Ile Met Gly Asn Arg Asp Gly Ile Asp Glu Met Ser Ser Thr Asn
        515                 520                 525
Ala Ser Val Leu Leu Ser Val Leu Lys Leu Ile Asp Lys Tyr Asp Leu
    530                 535                 540
Tyr Gly Gln Val Ala Tyr Pro Lys His His Lys Gln Tyr Asp Val Pro
545                 550                 555                 560
Asp Ile Tyr Arg Leu Ala Ala Lys Thr Lys Gly Val Phe Ile Asn Pro
                565                 570                 575
Ala Phe Ile Glu Pro Phe Gly Leu Thr Leu Ile Glu Ala Ala His
            580                 585                 590
Gly Leu Pro Ile Val Asp Thr Lys Asn Gly Gly Pro Val Asp Ile His
        595                 600                 605
Arg Val Leu Asp Asn Gly Leu Leu Val Asp Pro His Asp Gln Gln Ser
    610                 615                 620
Ile Ala Asp Ala Leu Leu Lys Leu Val Ser Asn Lys Gln Leu Trp Ala
625                 630                 635                 640
Lys Cys Arg Gln Asn Gly Leu Lys Asn Ile His Leu Phe Ser Trp Pro
                645                 650                 655
Glu His Cys Lys Thr Tyr Leu Ser Lys Ile Ala Thr Cys Lys Pro Arg
            660                 665                 670
His Pro Gln Trp Gln Arg Ser Glu Asp Gly Gly Glu Ser Ser Glu Ser
        675                 680                 685
Asp Ser Pro Gly Asp Ser Leu Arg Asp Leu Gln Asp Leu Ser Leu Asn
    690                 695                 700
Leu Lys Phe Ser Leu Asp Gly Glu Lys Ser Glu Gly Ser Gly Asn Asp
705                 710                 715                 720
Asn Ser Leu Asn Ser Asp Gly Asn Ala Ala Asp Arg Gly Ala Lys Leu
                725                 730                 735
Glu Asn Ala Val Leu Ser Trp Ser Lys Gly Ile Ser Lys Asp Thr Arg
            740                 745                 750
Arg Gly Gly Ala Thr Glu Lys Ser Asp Gln Asn Pro Asn Ala Gly Lys
        755                 760                 765
Phe Pro Pro Leu Arg Arg Arg Lys His Leu Phe Val Ile Ala Val Asp
    770                 775                 780
Cys Asp Thr Thr Ser Ser Leu Leu Glu Thr Ile Lys Ala Ile Phe Glu
785                 790                 795                 800
Ser Ala Gly Lys Asp Arg Ala Glu Ser Ile Val Gly Phe Ile Leu Ser
                805                 810                 815
Thr Ser Leu Thr Ile Ser Glu Ile Gln Ser Phe Leu Ile Ser Gly Gly
            820                 825                 830
Leu Ser Pro Ile Asp Phe Asp Ala Tyr Ile Cys Asn Ser Gly Ser Asp
        835                 840                 845
Leu Tyr Tyr Pro Ser Leu Asn Pro Gly Asp Arg Pro Phe Val Val Asp
    850                 855                 860
```

-continued

| | | | | | | | | | | | |
|---|---|---|---|---|---|---|---|---|---|---|---|
|Leu|Tyr|Tyr|His|Ser|His|Ile|Glu|Tyr|Arg|Trp|Gly Gly Glu Gly Leu|
|865| | | |870| | | |875| | |880|

Arg Lys Thr Leu Val Arg Trp Ala Asp Ser Ile Thr Asp Lys Gly
                885                 890                 895

Asp Asn Asp Glu Gln Ile Val Ser Pro Ala Glu Gln Leu Ser Thr Asp
            900                 905                 910

Tyr Cys Tyr Ala Phe Lys Val Arg Lys Pro Gly Met Ala Pro Pro Val
            915                 920                 925

Lys Glu Leu Arg Lys Leu Leu Arg Ile Gln Ala Leu Arg Cys His Pro
        930                 935                 940

Ile Tyr Cys Gln Asn Gly Thr Arg Leu Asn Val Ile Pro Val Leu Ala
945                 950                 955                 960

Ser Arg Ser Gln Ala Leu Arg Tyr Leu Tyr Val Arg Trp Gly Phe Glu
                965                 970                 975

Leu Ser Lys Met Val Val Phe Val Gly Glu Cys Gly Asp Thr Asp Tyr
            980                 985                 990

Glu Gly Leu Leu Gly Gly Leu His Lys Ser Val Ile Leu Lys Gly Val
        995                 1000                1005

Gly Ser Ser Ala Ile Ser Gln Leu His Asn Asn Arg Ser Tyr Pro Leu
    1010                1015                1020

Ser Asp Val Thr Pro Leu Asp Ser Pro Asn Ile Val Glu Ala Thr Glu
1025                1030                1035                1040

Gly Ser Ser Gly Ala Asp Ile Gln Ala Leu Ile Glu Lys Val Gly Tyr
                1045                1050                1055

Leu Asn Gly

<210> SEQ ID NO 17
<211> LENGTH: 646
<212> TYPE: DNA
<213> ORGANISM: Glycine max
<220> FEATURE:
<221> NAME/KEY: unsure
<222> LOCATION: (355)
<221> NAME/KEY: unsure
<222> LOCATION: (397)
<221> NAME/KEY: unsure
<222> LOCATION: (412)
<221> NAME/KEY: unsure
<222> LOCATION: (539)
<221> NAME/KEY: unsure
<222> LOCATION: (552)
<221> NAME/KEY: unsure
<222> LOCATION: (560)
<221> NAME/KEY: unsure
<222> LOCATION: (594)
<221> NAME/KEY: unsure
<222> LOCATION: (598)
<221> NAME/KEY: unsure
<222> LOCATION: (613)
<221> NAME/KEY: unsure
<222> LOCATION: (631)
<221> NAME/KEY: unsure
<222> LOCATION: (633)

<400> SEQUENCE: 17
aaacagtaga gttcctaaca tcaggcaatg ttcaagtgaa tgagtttgat gctttaattt     60
gcagtagtgg aagtcaagtt tactaccctg gcatcaatac agaagaagga aagcttttgc    120
ctgatccaga ttatgaggta catattgact atcgttgggg gtgtgaaggt cttaagaaaa    180
ccatttggaa actatgaat ggtgatgaga acagccccat tgaggaagat ctcaaatcca     240
gcaatgcaca ttgcatctca tacaaaataa aggatcttag taaggcaaaa aaagttgatg    300

```
agttgaggca gaagcttagg atgagaggtc tacgttgtca tcctatgtac tgcangggt      360 catctagaat gcatgtgatt cctcctcttg catctanagc ccaagcactc angtatccct      420
tgtacgttgg aggttgaacg ttgcaaacat gtactcaccc ttggagaaac ggggacacgg      480
attatgagga gatgattctg aacccacaa gaccataatc atgaaggaat ggttctaang      540
gtcaaaagag tnctaagagn ccaggaacta caaagagatg tattgcccaa tganaccncc      600
tgtgcatcat tcnaacacca tgaaacatgc nancttgaca attcaa                    646
```

<210> SEQ ID NO 18
<211> LENGTH: 136
<212> TYPE: PRT
<213> ORGANISM: Glycine max
<220> FEATURE:
<221> NAME/KEY: UNSURE
<222> LOCATION: (116)
<221> NAME/KEY: UNSURE
<222> LOCATION: (130)
<221> NAME/KEY: UNSURE
<222> LOCATION: (135)

<400> SEQUENCE: 18

```
Glu Phe Leu Thr Ser Gly Asn Val Gln Val Asn Glu Phe Asp Ala Leu
 1               5                  10                  15

Ile Cys Ser Ser Gly Ser Gln Val Tyr Tyr Pro Gly Ile Asn Thr Glu
            20                  25                  30

Glu Gly Lys Leu Leu Pro Asp Pro Asp Tyr Glu Val His Ile Asp Tyr
        35                  40                  45

Arg Trp Gly Cys Glu Gly Leu Lys Lys Thr Ile Trp Lys Leu Met Asn
50                  55                  60

Gly Asp Glu Asn Ser Pro Ile Glu Glu Asp Leu Lys Ser Ser Asn Ala
65                  70                  75                  80

His Cys Ile Ser Tyr Lys Ile Lys Asp Leu Ser Lys Ala Lys Lys Val
                85                  90                  95

Asp Glu Leu Arg Gln Lys Leu Arg Met Arg Gly Leu Arg Cys His Pro
            100                 105                 110

Met Tyr Cys Xaa Gly Ser Ser Arg Met His Val Ile Pro Pro Leu Ala
        115                 120                 125

Ser Xaa Ala Gln Ala Leu Xaa Tyr
    130                 135
```

<210> SEQ ID NO 19
<211> LENGTH: 1445
<212> TYPE: DNA
<213> ORGANISM: Triticum aestivum

<400> SEQUENCE: 19

```
gcatcacaaa cactcagaag ttcttgatat ttatcgttta gcagcgagaa cgaagggtgc      60
ttttgtaaat gtagcttact tgaacaatt cggtgttacc ttgatagagg ctgccatgca      120
tggtttacct gtaattgcaa caaaaaatgg agctcctgtt gaaattcatc aggtgctcaa      180
caatggtctc cttgtcgatc cacatgatca gaatgccatt gcagatgcac tgtataaact      240
tctttccgag aagcaacttt ggtcaaggtg cagagaaaat ggactaaaaa atattcacca      300
attttcctgg cctgaacatt gcaagaatca cctgtcaagg atattgactc ttggcatgag      360
atctcctgct gtcggtagcg aagaggaaag gagtaaggca cctatatcag gaaggaagca      420
tatcattgtt atttctgtag actctgttaa caaggagaat ctagtgcgga tcatcagaaa      480
```

-continued

```
tgcgattgag gccgcacata cagaaaacac accggcttca actggtttcg tgctgtcaac    540
ttcgctaaca atatcagaga tatgttcact gctagtatct gtaggcatgc atcctgctgg    600
ttttgatgct ttcatctgca acagtgggag tagcatttac tatccttcat attctggtaa    660
tacgccaagc aattccaagg ttacccatgt aatagatcga atcatcaat cacatattga     720 gtatcgttgg ggaggagaag gtctaagaaa gtatcttgtg aaatgggcta cttcagtggt    780
tgaaagaaag ggaagaattg aaaggcaaat gattttttgaa gattcagaac actcttctac   840
atattgtctt gcatttaaag tggtgattcc gattacgaag agctgctagg gggtctccac    900
aggaccataa tcctgaaggg cgacttcaac attgctgcaa acagaatcca cagtccgg      960 agataccect tgcaggatgt cgttgcactg acagctcca acatcatcga agtccagggt    1020
tgcactacag aggacatcaa gtctgccctg cgtcagattg tgtgccgac acaataacat    1080 ctttgcgcgc accacacgaa aaggaagaag aaaaggagag gaagaacgag ccaaaccgag   1140
cgccactatt tccatacctg atgggaatgt cgattttgtt tgtagattgt agagtgtggg   1200
tgtggtatat tctcgagctg tgaataactt ccaccttttg tttgtactat tcacaaattt   1260
tgaagtggac aatatcgata aatgtagtgg gaaaacaaat gtgagcagaa aagtcatttg   1320
ggaactgaga tgccccgaaa atacagacaa ggcgggagcc taaatggatt aactctgtct   1380
actcgtttta ctggcaaaaa aaaaaaaaaa aaaaaaaaaa aaaaaaaaaa aaaaaaaaaa   1440
aaaaa                                                               1445
```

<210> SEQ ID NO 20
<211> LENGTH: 358
<212> TYPE: PRT
<213> ORGANISM: Triticum aestivum
<220> FEATURE:
<221> NAME/KEY: UNSURE
<222> LOCATION: (286)

<400> SEQUENCE: 20

```
His His Lys His Ser Glu Val Leu Asp Ile Tyr Arg Leu Ala Ala Arg
 1               5                  10                  15

Thr Lys Gly Ala Phe Val Asn Val Ala Tyr Phe Glu Gln Phe Gly Val
            20                  25                  30

Thr Leu Ile Glu Ala Ala Met His Gly Leu Pro Val Ile Ala Thr Lys
        35                  40                  45

Asn Gly Ala Pro Val Glu Ile His Gln Val Leu Asn Asn Gly Leu Leu
    50                  55                  60

Val Asp Pro His Asp Gln Asn Ala Ile Ala Asp Ala Leu Tyr Lys Leu
65                  70                  75                  80

Leu Ser Glu Lys Gln Leu Trp Ser Arg Cys Arg Glu Asn Gly Leu Lys
                85                  90                  95

Asn Ile His Gln Phe Ser Trp Pro Glu His Cys Lys Asn His Leu Ser
            100                 105                 110

Arg Ile Leu Thr Leu Gly Met Arg Ser Pro Ala Val Gly Ser Glu Glu
        115                 120                 125

Glu Arg Ser Lys Ala Pro Ile Ser Gly Arg Lys His Ile Ile Val Ile
    130                 135                 140

Ser Val Asp Ser Val Asn Lys Glu Asn Leu Val Arg Ile Ile Arg Asn
145                 150                 155                 160

Ala Ile Glu Ala Ala His Thr Glu Asn Thr Pro Ala Ser Thr Gly Phe
                165                 170                 175

Val Leu Ser Thr Ser Leu Thr Ile Ser Glu Ile Cys Ser Leu Leu Val
```

-continued

```
                    180                 185                 190
Ser Val Gly Met His Pro Ala Gly Phe Asp Ala Phe Ile Cys Asn Ser
            195                 200                 205

Gly Ser Ser Ile Tyr Tyr Pro Ser Tyr Ser Gly Asn Thr Pro Ser Asn
210                 215                 220

Ser Lys Val Thr His Val Ile Asp Arg Asn His Gln Ser His Ile Glu
225                 230                 235                 240

Tyr Arg Trp Gly Gly Glu Gly Leu Arg Lys Tyr Leu Val Lys Trp Ala
                245                 250                 255

Thr Ser Val Val Glu Arg Lys Gly Arg Ile Glu Arg Gln Met Ile Phe
            260                 265                 270

Glu Asp Ser Glu His Ser Ser Thr Tyr Cys Leu Ala Phe Xaa Ser Gly
            275                 280                 285

Asp Ser Asp Tyr Glu Glu Leu Leu Gly Gly Leu His Arg Thr Ile Ile
290                 295                 300

Leu Lys Gly Asp Phe Asn Ile Ala Ala Asn Arg Ile His Thr Val Arg
305                 310                 315                 320

Arg Tyr Pro Leu Gln Asp Val Val Ala Leu Asp Ser Ser Asn Ile Ile
                325                 330                 335

Glu Val Gln Gly Cys Thr Thr Glu Asp Ile Lys Ser Ala Leu Arg Gln
            340                 345                 350

Ile Gly Val Pro Thr Gln
            355

<210> SEQ ID NO 21
<211> LENGTH: 1660
<212> TYPE: DNA
<213> ORGANISM: Triticum aestivum
<220> FEATURE:
<221> NAME/KEY: unsure
<222> LOCATION: (1323)
<221> NAME/KEY: unsure
<222> LOCATION: (1339)
<221> NAME/KEY: unsure
<222> LOCATION: (1393)
<221> NAME/KEY: unsure
<222> LOCATION: (1418)
<221> NAME/KEY: unsure
<222> LOCATION: (1453)
<221> NAME/KEY: unsure
<222> LOCATION: (1523)
<221> NAME/KEY: unsure
<222> LOCATION: (1530)
<221> NAME/KEY: unsure
<222> LOCATION: (1541)
<221> NAME/KEY: unsure
<222> LOCATION: (1560)
<221> NAME/KEY: unsure
<222> LOCATION: (1576)
<221> NAME/KEY: unsure
<222> LOCATION: (1579)
<221> NAME/KEY: unsure
<222> LOCATION: (1592)
<221> NAME/KEY: unsure
<222> LOCATION: (1599)
<221> NAME/KEY: unsure
<222> LOCATION: (1603)
<221> NAME/KEY: unsure
<222> LOCATION: (1614)
<221> NAME/KEY: unsure
<222> LOCATION: (1621)
<221> NAME/KEY: unsure
<222> LOCATION: (1631)

<400> SEQUENCE: 21
gcacgagccg ctgcttatgg tctgcccgtg gtggcaacca agaacggcgg gccggtggac     60
```

-continued

```
atcctcaagg cgcttcacaa cggcctgctg gtggacccgc actccgccga ggcgatcacc    120
ggcgcgctgc tcagcctgct ggccgacaag gggcagtggc tggagagccg acgcaacggc    180
ctgcgcaaca tccaccgctt ctcgtggccg caccactgcc gcctctacct ctcccacgtc    240
gccgcctact gcgaccaccc gtcgccgcac cagcggctcc gcgtccctgg cgtcccgtct    300
gcctcggcga gcatgggcgg tgacgactcc ctctcggact cactccgtgg cctctcgctc    360
caaatctccg tggacgcctc caacgacctc aatgccgggg actcggccgc gctgatcatg    420
gacgccctac gccgccgccc ggcggccgac aggcgcgagg gctccggcag ggcgttgggc    480
ttcgcgccgg aaggaggca gaggctcctt gtcgtcgccg tcgactgcta cggcgatgac    540
ggcaagcccg acgtcgagca actgaagaaa gccatcgacg cggcgatgtc cgccagtgac    600
ggcgcgggag ggcggcaggg gtacgtgctc tcgaccggca tgaccatccc cgagaccgcg    660
gagacgctca aggcctgcgg cgccgacccg gccggcttcg acgcgctcat ttgcagcagc    720
ggcgcggaga tatgctaccc gtggaaggag ctgacggccg acgaggagta ctccggccac    780
gtggcgttcc ggtggcccgg cgaccacgtg aaaaccgtcg tgccgaggct cgggaaggcc    840
gacgacgcgc aggcgtccga cctcgccgtc gacgtgtccg ctggctccgt gcactgccac    900
gcctacgccg ccaccgacgc gtccaaggtg aagaaggtgg attcgatcag gcaggcgctg    960
cggatgcgcg ggttccggtg caacctcgtc tacacgcgcg cgtgcacgcg cctcaacgtc   1020
atccctctct ccgcttcccg cccacgcgcg ttgaggtacc tgtcgataca gtggggcatc   1080
gatctcgcca aggtggcggt gctcgtcggc gagaccggga caccgaccg cgagaagctc   1140
ctgccggggc tgcacaagac gataactcct gccggggatg ctctcccaac ggcagcgaag   1200
cacctcgacc ccgacgagga cgagtacccc acccaggacg tcgtgcccat gactcaccca   1260
aacatcatca caatcggccg aagcccagcc tggcttttct aatttgacgc ggccgagaaa   1320
cantccgtac ggccgtacnc actgtaatcc tgggcaggaa gatgactgcc agaaaagtat   1380
aataaatttt aangatgtgc aaccatgaca acatgggnta aattttttagt ctaacatctc   1440
ccttcctgag gcnttgtcat atatatcact tataatgaac caagaaagaa tgcatgtgaa   1500
aaaacgatac aaactaactc tcncttaaan ctttggttaa natttgagat tctcacgtgn   1560
tcgtgactcg gtaaangant cggaaatttc cnattgacnc agnaccccg ccancccct   1620
ngccccggtg nctaaaaggg ggaatttggg cccgaatccg                        1660
```

<210> SEQ ID NO 22
<211> LENGTH: 433
<212> TYPE: PRT
<213> ORGANISM: Triticum aestivum

<400> SEQUENCE: 22

```
Ala Arg Ala Ala Ala Tyr Gly Leu Pro Val Val Ala Thr Lys Asn Gly
 1               5                  10                  15

Gly Pro Val Asp Ile Leu Lys Ala Leu His Asn Gly Leu Leu Val Asp
            20                  25                  30

Pro His Ser Ala Glu Ala Ile Thr Gly Ala Leu Leu Ser Leu Leu Ala
        35                  40                  45

Asp Lys Gly Gln Trp Leu Glu Ser Arg Arg Asn Gly Leu Arg Asn Ile
    50                  55                  60

His Arg Phe Ser Trp Pro His His Cys Arg Leu Tyr Leu Ser His Val
65                  70                  75                  80

Ala Ala Tyr Cys Asp His Pro Ser Pro His Gln Arg Leu Arg Val Pro
```

```
                        85                  90                  95
Gly Val Pro Ser Ala Ser Ala Ser Met Gly Gly Asp Asp Ser Leu Ser
            100                 105                 110

Asp Ser Leu Arg Gly Leu Ser Leu Gln Ile Ser Val Asp Ala Ser Asn
            115                 120                 125

Asp Leu Asn Ala Gly Asp Ser Ala Ala Leu Ile Met Asp Ala Leu Arg
            130                 135                 140

Arg Arg Pro Ala Ala Asp Arg Arg Glu Gly Ser Gly Arg Ala Leu Gly
145                 150                 155                 160

Phe Ala Pro Gly Arg Arg Gln Arg Leu Leu Val Val Ala Val Asp Cys
                165                 170                 175

Tyr Gly Asp Asp Gly Lys Pro Asp Val Glu Gln Leu Lys Lys Ala Ile
                180                 185                 190

Asp Ala Ala Met Ser Ala Ser Asp Gly Ala Gly Gly Arg Gln Gly Tyr
                195                 200                 205

Val Leu Ser Thr Gly Met Thr Ile Pro Glu Thr Ala Glu Thr Leu Lys
            210                 215                 220

Ala Cys Gly Ala Asp Pro Ala Gly Phe Asp Ala Leu Ile Cys Ser Ser
225                 230                 235                 240

Gly Ala Glu Ile Cys Tyr Pro Trp Lys Glu Leu Thr Ala Asp Glu Glu
                245                 250                 255

Tyr Ser Gly His Val Ala Phe Arg Trp Pro Gly Asp His Val Lys Thr
                260                 265                 270

Val Val Pro Arg Leu Gly Lys Ala Asp Ala Gln Ala Ser Asp Leu
            275                 280                 285

Ala Val Asp Val Ser Ala Gly Ser Val His Cys His Ala Tyr Ala Ala
            290                 295                 300

Thr Asp Ala Ser Lys Val Lys Lys Val Asp Ser Ile Arg Gln Ala Leu
305                 310                 315                 320

Arg Met Arg Gly Phe Arg Cys Asn Leu Val Tyr Thr Arg Ala Cys Thr
                325                 330                 335

Arg Leu Asn Val Ile Pro Leu Ser Ala Ser Arg Pro Arg Ala Leu Arg
                340                 345                 350

Tyr Leu Ser Ile Gln Trp Gly Ile Asp Leu Ala Lys Val Ala Val Leu
                355                 360                 365

Val Gly Glu Thr Gly Asp Thr Asp Arg Glu Lys Leu Leu Pro Gly Leu
            370                 375                 380

His Lys Thr Ile Thr Pro Ala Gly Asp Ala Leu Pro Thr Ala Ala Lys
385                 390                 395                 400

His Leu Asp Pro Asp Glu Asp Glu Tyr Pro Thr Gln Asp Val Val Pro
                405                 410                 415

Met Thr His Pro Asn Ile Ile Thr Ile Gly Arg Ser Pro Ala Trp Leu
                420                 425                 430

Phe

<210> SEQ ID NO 23
<211> LENGTH: 3623
<212> TYPE: DNA
<213> ORGANISM: Zea mays

<400> SEQUENCE: 23
ttcggcacga gcagaaacct ccaggatccg actccaatcg aatcgccaaa gcagacaggg      60
gcgctcgcgg gggcgccgag ctcgacgggg cgagatggcc gggaacgact ggatcaacag     120
```

-continued

```
ctacctggag gctattctgg acgctggcgg ggccgcggga gatctctcgg cagccgcagg      180
cagcggggac ggccgcgacg ggacggccgt ggagaagcgg gataagtcgt cgctgatgct      240
ccgagagcgc ggccggttca gccccgcgcg atacttcgtc gaggaggtca tctccggctt      300
cgacgagacc gacctctaca agacctgggt ccgcacctcg gctatgagga gtccccagga      360
gcggaacacg cggctggaga acatgtcgtg gaggatctgg aacctcgcca ggaagaagaa      420
gcagatagaa ggagaggaag cctcacgatt gtctaaacaa cgcatggaat ttgagaaagc      480
tcgtcaatat gctgctgatt tgtctgaaga cctatctgaa ggagaaaagg gagaaacaaa      540
taatgaacca tctattcatg atgagagcat gaggacgcgg atgccaagga ttggttcaac      600
tgatgctatt gatacatggg caaaccagca caaagataaa agttgtaca tagtattgat       660 aagcattcat ggtcttatac gcggggagaa tatggagctg ggacgtgatt cagatacagt      720
gaaatatgtt gtagaacttg ctagggcttt aggttcaaca ccaggagtat acagagtgga      780
tctactaaca aggcagattt ctgcacctga tgttgattgg agttatgggg aacctactga      840
gatgctcagt ccaataagtt cagaaaactt tgggcttgag ctgggcgaaa gcagtggtgc      900
ctatattgtc cggataccat tcggaccaag agacaaatat atccctaaag agcatctatg      960
gcctcacatc caggaatttg ttgatggcgc acttgtccat atcatgcaga tgtccaaggt     1020
ccttggagaa caaattggta gtgggcaacc agtatggcct gttgttatac atggacacta     1080
tgctgatgct ggtgattctg ctgctttact gtctggggca ctcaatgtac ccatggtatt     1140
cactggtcat tctcttggca gagataagtt ggaccagatt ttgaagcaag gcgtcaaac      1200 cagggatgaa ataaatgcaa cctataagat aatgcgtcga attgaggccg aggaactttg     1260
ccttgataca tctgaaatca taattacaag taccaggcaa gaaatagaac agcaatgggg     1320
attatatgat ggttttgatc taactatggc ccggaaactc agagcaagaa taaggcgtgg     1380
tgtgagctgc tttggtcgtt acatgccccg tatgattgca atccctcctg gcatggagtt     1440
tagtcatata gcaccacatg atgttgacct cgacagtgag gaaggaaatg gagatggctc     1500
aggttcacca gatccaccta tttgggctga tataatgcgc ttcttctcaa accccccggaa    1560 gccaatgatt cttgctcttg ctcgtccgga tccgaagaag aatatcacta ctctagtcaa     1620
agcatttggt gaacatcgtg aactgagaaa tttagcaaat cttacactga tcatggggaa     1680
tcgtgatgtc attgatgaaa tgtcaagcac aaatgcagct gttttgactt cagcactcaa     1740
gttaattgat aaatatgatc tatatggaca agtggcatac cccaagcacc ataagcaatc     1800
tgaagttcct gatatttatc gtttagctgc gagaacaaaa ggagttttta tcaattgtgc     1860
attggttgaa ccatttggac tcaccttgat tgaggctgct gcatatggtc tacccatggt     1920
tgccacccga aatggtgggc tgtggacat acatcgggtt cttgataatg gaattcttgt      1980
tgacccccac aatcaaaatg aaatagctga ggcactttat aagcttgtgt cagataagca     2040
cttgtggtca caatgtcgcc agaatggtct gaaaaacatc cataaatttt catggcctga     2100
acattgccag aactatttgg cacgtgtagt cactctcaag cctagacatc cccgctggca     2160
aaagaatgat gttgcagctg aaatatctga agcagattca cccgaggact ctctgaggga     2220
tattcatgac atatcactta acttaaagct ttccttggac agtgaaaaat caggcagcaa     2280 agaaggggaat tcaaatgctt tgagaaggca ttttgaggat gcagcgcaaa agttgtcagg    2340
tgttaatgac atcaaaaagg atgtgccagg tgagaatggt aagtggtcgt cattgcgtag     2400
gaggaagcac atcattgtaa ttgctgtaga ctctgtgcaa gatgcagact tgttcaggt     2460 tattaaaaat atttttgaag cttcaagaaa tgagagatca agtggtgctg ttggttttgt     2520
```

-continued

```
gttgtcaacg gctagagcaa tatcagagtt acatactttg cttatatctg gagggataga    2580
agctagtgac tttgatgcct tcatatgcaa cagtggcagt gatctttgtt atccatcttc    2640
aagctctgag gacatgctta accctgctga gctcccattc atgattgatc ttgattatca    2700
ctcccaaatt gaatatcgct ggggaggaga aggtttaagg aagacattaa ttcgttgggc    2760
agctgagaaa aacaaagaaa gtggacaaaa aatatttatt gaggatgaag aatgctcatc    2820
cacctactgc atttcattta aagtgtccaa tactgcagct gcacctcctg tgaaggagat    2880
taggaggaca atgagaatac aagcactgcg ttgccatgtt ttgtacagcc atgatggtag    2940
caagttgaat gtaattcctg ttttggcttc tcgctcacag gctttaaggt atttgtatat    3000
ccgatggggg gtagagctgt caaacatcac cgtgattgtc ggtgagtgtg gtgacacaga    3060
ttatgaagga ctacttggag gcgtgcacaa aactatcata ctcaaaggct cgttcaatac    3120
tgctccaaac caagttcatg ctaacagaag ctattcatcc aagatgttg tatcctttga     3180 caaacaagga attgcttcaa ttgagggata tggtccagac aatctaaagt cagctctacg    3240
gcaatttggt atattgaaag actaaatctt tgatctttgc tggtcagcag aggaatcaaa    3300
gcaggaatgt aggatcgagg agagtgacag gacttcccct ctgtgcactt cgccgaaaag    3360
taataatggg attgctatgc atggcccttg ttgtacattg gaaaattggg cacgcaaact    3420
tgtgtcagtt ttcccgtttt tgggaaattc attgatggtg ttttgtaac tataccaacc    3480 tgtgtcagtt ttgccgttgt tgcaaaactc agtgatggtg tttttttgtaa ttattataca   3540 tccgaataat aagactggtg tttcccgtca caaaaaaaa aaaaaaaaa aaaaaaaaa       3600 aaaaaaaaaa aaaaaaaaa aaa                                              3623
```

<210> SEQ ID NO 24
<211> LENGTH: 1087
<212> TYPE: PRT
<213> ORGANISM: Zea mays

<400> SEQUENCE: 24

```
Ser Ala Arg Ala Glu Thr Ser Arg Ile Arg Leu Gln Ser Asn Arg Gln
  1               5                  10                  15

Ser Arg Gln Gly Arg Ser Arg Gly Arg Arg Ala Arg Arg Gly Glu Met
             20                  25                  30

Ala Gly Asn Asp Trp Ile Asn Ser Tyr Leu Glu Ala Ile Leu Asp Ala
         35                  40                  45

Gly Gly Ala Ala Gly Asp Leu Ser Ala Ala Gly Ser Gly Asp Gly
     50                  55                  60

Arg Asp Gly Thr Ala Val Glu Lys Arg Asp Lys Ser Ser Leu Met Leu
 65                  70                  75                  80

Arg Glu Arg Gly Arg Phe Ser Pro Ala Arg Tyr Phe Val Glu Val
                 85                  90                  95

Ile Ser Gly Phe Asp Glu Thr Asp Leu Tyr Lys Thr Trp Val Arg Thr
            100                 105                 110

Ser Ala Met Arg Ser Pro Gln Glu Arg Asn Thr Arg Leu Glu Asn Met
        115                 120                 125

Ser Trp Arg Ile Trp Asn Leu Ala Arg Lys Lys Gln Ile Glu Gly
    130                 135                 140

Glu Glu Ala Ser Arg Leu Ser Lys Gln Arg Met Glu Phe Lys Ala
145                 150                 155                 160

Arg Gln Tyr Ala Ala Asp Leu Ser Glu Asp Leu Ser Glu Gly Glu Lys
                165                 170                 175
```

-continued

```
Gly Glu Thr Asn Asn Glu Pro Ser Ile His Asp Glu Ser Met Arg Thr
            180                 185                 190

Arg Met Pro Arg Ile Gly Ser Thr Asp Ala Ile Asp Thr Trp Ala Asn
        195                 200                 205

Gln His Lys Asp Lys Leu Tyr Ile Val Leu Ile Ser Ile His Gly
    210                 215                 220

Leu Ile Arg Gly Glu Asn Met Glu Leu Gly Arg Asp Ser Asp Thr Val
225                 230                 235                 240

Lys Tyr Val Val Glu Leu Ala Arg Ala Leu Gly Ser Thr Pro Gly Val
                245                 250                 255

Tyr Arg Val Asp Leu Leu Thr Arg Gln Ile Ser Ala Pro Asp Val Asp
                260                 265                 270

Trp Ser Tyr Gly Glu Pro Thr Glu Met Leu Ser Pro Ile Ser Ser Glu
            275                 280                 285

Asn Phe Gly Leu Glu Leu Gly Glu Ser Ser Gly Ala Tyr Ile Val Arg
    290                 295                 300

Ile Pro Phe Gly Pro Arg Asp Lys Tyr Ile Pro Lys Glu His Leu Trp
305                 310                 315                 320

Pro His Ile Gln Glu Phe Val Asp Gly Ala Leu Val His Ile Met Gln
                325                 330                 335

Met Ser Lys Val Leu Gly Glu Gln Ile Gly Ser Gly Gln Pro Val Trp
            340                 345                 350

Pro Val Val Ile His Gly His Tyr Ala Asp Ala Gly Asp Ser Ala Ala
        355                 360                 365

Leu Leu Ser Gly Ala Leu Asn Val Pro Met Val Phe Thr Gly His Ser
    370                 375                 380

Leu Gly Arg Asp Lys Leu Asp Gln Ile Leu Lys Gln Gly Arg Gln Thr
385                 390                 395                 400

Arg Asp Glu Ile Asn Ala Thr Tyr Lys Ile Met Arg Arg Ile Glu Ala
                405                 410                 415

Glu Glu Leu Cys Leu Asp Thr Ser Glu Ile Ile Ile Thr Ser Thr Arg
            420                 425                 430

Gln Glu Ile Glu Gln Gln Trp Gly Leu Tyr Asp Gly Phe Asp Leu Thr
        435                 440                 445

Met Ala Arg Lys Leu Arg Ala Arg Ile Arg Arg Gly Val Ser Cys Phe
    450                 455                 460

Gly Arg Tyr Met Pro Arg Met Ile Ala Ile Pro Pro Gly Met Glu Phe
465                 470                 475                 480

Ser His Ile Ala Pro His Asp Val Asp Leu Asp Ser Glu Glu Gly Asn
                485                 490                 495

Gly Asp Gly Ser Gly Ser Pro Asp Pro Pro Ile Trp Ala Asp Ile Met
            500                 505                 510

Arg Phe Phe Ser Asn Pro Arg Lys Pro Met Ile Leu Ala Leu Ala Arg
        515                 520                 525

Pro Asp Pro Lys Lys Asn Ile Thr Thr Leu Val Lys Ala Phe Gly Glu
    530                 535                 540

His Arg Glu Leu Arg Asn Leu Ala Asn Leu Thr Leu Ile Met Gly Asn
545                 550                 555                 560

Arg Asp Val Ile Asp Glu Met Ser Ser Thr Asn Ala Ala Val Leu Thr
                565                 570                 575

Ser Ala Leu Lys Leu Ile Asp Lys Tyr Asp Leu Tyr Gly Gln Val Ala
            580                 585                 590
```

-continued

```
Tyr Pro Lys His His Lys Gln Ser Glu Val Pro Asp Ile Tyr Arg Leu
        595                 600                 605
Ala Ala Arg Thr Lys Gly Val Phe Ile Asn Cys Ala Leu Val Glu Pro
    610                 615                 620
Phe Gly Leu Thr Leu Ile Glu Ala Ala Tyr Gly Leu Pro Met Val
625                 630                 635                 640
Ala Thr Arg Asn Gly Gly Pro Val Asp Ile His Arg Val Leu Asp Asn
                645                 650                 655
Gly Ile Leu Val Asp Pro His Asn Gln Asn Glu Ile Ala Glu Ala Leu
            660                 665                 670
Tyr Lys Leu Val Ser Asp Lys His Leu Trp Ser Gln Cys Arg Gln Asn
        675                 680                 685
Gly Leu Lys Asn Ile His Lys Phe Ser Trp Pro Glu His Cys Gln Asn
    690                 695                 700
Tyr Leu Ala Arg Val Val Thr Leu Lys Pro Arg His Pro Arg Trp Gln
705                 710                 715                 720
Lys Asn Asp Val Ala Ala Glu Ile Ser Glu Ala Asp Ser Pro Glu Asp
                725                 730                 735
Ser Leu Arg Asp Ile His Asp Ile Ser Leu Asn Leu Lys Leu Ser Leu
            740                 745                 750
Asp Ser Glu Lys Ser Gly Ser Lys Glu Gly Asn Ser Asn Ala Leu Arg
        755                 760                 765
Arg His Phe Glu Asp Ala Ala Gln Lys Leu Ser Gly Val Asn Asp Ile
    770                 775                 780
Lys Lys Asp Val Pro Gly Glu Asn Gly Lys Trp Ser Ser Leu Arg Arg
785                 790                 795                 800
Arg Lys His Ile Ile Val Ile Ala Val Asp Ser Val Gln Asp Ala Asp
                805                 810                 815
Phe Val Gln Val Ile Lys Asn Ile Phe Glu Ala Ser Arg Asn Glu Arg
            820                 825                 830
Ser Ser Gly Ala Val Gly Phe Val Leu Ser Thr Ala Arg Ala Ile Ser
        835                 840                 845
Glu Leu His Thr Leu Leu Ile Ser Gly Gly Ile Glu Ala Ser Asp Phe
    850                 855                 860
Asp Ala Phe Ile Cys Asn Ser Gly Ser Asp Leu Cys Tyr Pro Ser Ser
865                 870                 875                 880
Ser Ser Glu Asp Met Leu Asn Pro Ala Glu Leu Pro Phe Met Ile Asp
                885                 890                 895
Leu Asp Tyr His Ser Gln Ile Glu Tyr Arg Trp Gly Glu Gly Leu
            900                 905                 910
Arg Lys Thr Leu Ile Arg Trp Ala Ala Glu Lys Asn Lys Glu Ser Gly
        915                 920                 925
Gln Lys Ile Phe Ile Glu Asp Glu Glu Cys Ser Ser Thr Tyr Cys Ile
    930                 935                 940
Ser Phe Lys Val Ser Asn Thr Ala Ala Pro Pro Val Lys Glu Ile
945                 950                 955                 960
Arg Arg Thr Met Arg Ile Gln Ala Leu Arg Cys His Val Leu Tyr Ser
                965                 970                 975
His Asp Gly Ser Lys Leu Asn Val Ile Pro Val Leu Ala Ser Arg Ser
            980                 985                 990
Gln Ala Leu Arg Tyr Leu Tyr Ile Arg Trp Gly Val Glu Leu Ser Asn
        995                 1000                1005
Ile Thr Val Ile Val Gly Glu Cys Gly Asp Thr Asp Tyr Glu Gly Leu
```

Leu Gly Gly Val His Lys Thr Ile Ile Leu Lys Gly Ser Phe Asn Thr
1025                1030                1035                1040

Ala Pro Asn Gln Val His Ala Asn Arg Ser Tyr Ser Ser Gln Asp Val
            1045                1050                1055

Val Ser Phe Asp Lys Gln Gly Ile Ala Ser Ile Glu Gly Tyr Gly Pro
        1060                1065                1070

Asp Asn Leu Lys Ser Ala Leu Arg Gln Phe Gly Ile Leu Lys Asp
    1075                1080                1085

<210> SEQ ID NO 25
<211> LENGTH: 2455
<212> TYPE: DNA
<213> ORGANISM: Oryza sativa

<400> SEQUENCE: 25

| | | | | | |
|---|---|---|---|---|---|
| gcacgaggaa | gtgaagagct | tctcaagcaa | gggagacaga | caagggagca | aataaacatg | 60 |
| acatacaaaa | taatgtgtag | aattgaggca | gaggagttgg | ctcttgatgc | atctgaaata | 120 |
| gttatagcaa | gcactaggca | agagataaa | gagcaatgga | atttgtatga | cggttttgag | 180 |
| gtcatacttg | caaggaaact | ccgtgcaaga | gtcaagcgtg | gtgctaactg | ctatggtcgc | 240 |
| tatatgcctc | gtatggttat | cattcccca | ggtgttgaat | ttggccatat | gattcatgac | 300 |
| ttcgatatgg | atggtgagga | agacggtcca | tccccagcct | ctgaagatcc | atctatttgg | 360 |
| tccgagataa | tgcggttctt | tacaaaccct | aggaaaccta | tgattctggc | agttgctcgc | 420 |
| ccttatcctg | aaaagaatat | tactactctt | gtgaaggcgt | ttggtgagtg | ccgaccactg | 480 |
| agggagcttg | ctaatctaac | attgataatg | gaaaccgtg | aggctatttc | caagatgcat | 540 |
| aatatgagtg | cagctgtttt | gacatcagta | cttacattga | ttgatgaata | tgatttgtat | 600 |
| ggtcaagtgg | catacccaaa | gcgtcacaaa | cactcggaag | ttcctgatat | ttaccgttta | 660 |
| gcagtgagaa | caaagggtgc | ttttgtaaat | gtgccttact | ttgaacagtt | cggtgtcacc | 720 |
| ttgatagagg | ctgccatgca | tggtttgcct | gtaattgcaa | caaaaaatgg | agctcctgtt | 780 |
| gaaattcacc | aggtgctgga | caatggtctc | cttgttgatc | cccatgatca | gcatgcaatt | 840 |
| gcagatgcac | tctataaact | cctttctgaa | aaacaacttt | ggtcaaaatg | ccgagagaat | 900 |
| gggctgaaaa | atatacatca | gttttcttgg | cctgaacatt | gcaagaatta | cttgtcaagg | 960 |
| atatcaactc | ttggcccaag | gcatcctgct | tttgcaagca | atgaagaccg | gattaaggca | 1020 |
| cctattaagg | gaaggaagca | tgtcactgtt | attgctgtag | attctgtcag | taaggaagat | 1080 |
| ctgattcgca | ttgtcagaaa | ttctatcgag | gctgcacgta | agaaaaattt | gtcaggatcg | 1140 |
| acaggttttg | tgttgtcaac | ttccctgaca | ataggggaga | tacattctct | attaatgtct | 1200 |
| gctggcatgc | ttcctactgg | attcgatgct | ttcatatgca | atagtggaag | tgatttgtat | 1260 |
| tatccttcat | gtactggtga | tacaccaagc | aactcccgtg | ttacatttgc | attagatcgt | 1320 |
| agttaccaat | cacatataga | gtatcattgg | ggaggagaag | gtttaaggaa | atatctagtg | 1380 |
| aagtgggctt | cttccgtggt | agaaagaaga | gggaggattg | aaaaacaagt | tatcttcgaa | 1440 |
| gatccagagc | actcttcaac | atactgtctt | gcatttaaag | tggtcaatcc | aaatcattta | 1500 |
| cctcctttaa | aggagctgca | aaagttgatg | agaattcagt | cactccgttg | tcacgctctg | 1560 |
| tataaccatg | gtgctaccag | actatctgta | attccaatcc | acgcatcacg | gtctaaggct | 1620 |
| ctaaggtact | tatctgttcg | ctggggcata | gagttgcaaa | atgtggtggt | tcttgttggt | 1680 |
| gaaactggtg | attcagatta | cgaagaattg | tttggaggtc | ttcataagac | ggtcatcctt | 1740 |

-continued

```
aagggtgaat tcaacacatc tgcaaataga atccattctg ttaggcggta tcctttacaa    1800
gatgttgttg cacttgatag cccaaacatc attggaattg agggttatgg cactgatgac    1860
atgaggtctg ctctgaaaca actggatata cgggcacagt gacaccaagc ccccatctgt    1920
ttatcattaa tatatgaaga aaaccagtgg acgatacaaa gacagcaaac aaacactagc    1980
atttccatac ttgatggaga tgccgatttt gccatgtaag tcatgtagtt tatgtgtgtg    2040
gtccttgagc tgtgaatagc attccgaaat ctcatcccat tgagattttg gtatgtggca    2100
attttggagt aaaaatcgat tccatccagg aatacggaca aaagaaattg gttacaatgt    2160
tgataatgaa aaacatgtta aggaagcatt aattcagcaa gaaaagcttc caaaatcact    2220
acaattcttg gccaagcttg caatttccct tttttgaag tggaagctta tgttgtgtgt     2280
ttactgctgg gtggaccata tggccctggc agccttctt tactatgttt actccaggag    2340
ggctgcctag ctttcgtgta agtattgttt gacacgatgg ttcattctat atatccaaag    2400
ttttgttgag atcaaaaaaa aaaaaaaaaa aaaaaaaaa aaaaaaaaaa aaaaa         2455
```

<210> SEQ ID NO 26
<211> LENGTH: 633
<212> TYPE: PRT
<213> ORGANISM: Oryza sativa

<400> SEQUENCE: 26

```
Ala Arg Gly Ser Glu Glu Leu Leu Lys Gln Gly Arg Gln Thr Arg Glu
 1               5                  10                  15

Gln Ile Asn Met Thr Tyr Lys Ile Met Cys Arg Ile Glu Ala Glu Glu
            20                  25                  30

Leu Ala Leu Asp Ala Ser Glu Ile Val Ile Ala Ser Thr Arg Gln Glu
        35                  40                  45

Ile Glu Glu Gln Trp Asn Leu Tyr Asp Gly Phe Glu Val Ile Leu Ala
    50                  55                  60

Arg Lys Leu Arg Ala Arg Val Lys Arg Gly Ala Asn Cys Tyr Gly Arg
65                  70                  75                  80

Tyr Met Pro Arg Met Val Ile Pro Pro Gly Val Glu Phe Gly His
                85                  90                  95

Met Ile His Asp Phe Asp Met Asp Gly Glu Glu Asp Gly Pro Ser Pro
            100                 105                 110

Ala Ser Glu Asp Pro Ser Ile Trp Ser Glu Ile Met Arg Phe Phe Thr
        115                 120                 125

Asn Pro Arg Lys Pro Met Ile Leu Ala Val Ala Arg Pro Tyr Pro Glu
    130                 135                 140

Lys Asn Ile Thr Thr Leu Val Lys Ala Phe Gly Glu Cys Arg Pro Leu
145                 150                 155                 160

Arg Glu Leu Ala Asn Leu Thr Leu Ile Met Gly Asn Arg Glu Ala Ile
                165                 170                 175

Ser Lys Met His Asn Met Ser Ala Ala Val Leu Thr Ser Val Leu Thr
            180                 185                 190

Leu Ile Asp Glu Tyr Asp Leu Tyr Gly Gln Val Ala Tyr Pro Lys Arg
        195                 200                 205

His Lys His Ser Glu Val Pro Asp Ile Tyr Arg Leu Ala Val Arg Thr
    210                 215                 220

Lys Gly Ala Phe Val Asn Val Pro Tyr Phe Glu Gln Phe Gly Val Thr
225                 230                 235                 240

Leu Ile Glu Ala Ala Met His Gly Leu Pro Val Ile Ala Thr Lys Asn
```

```
                245                 250                 255
Gly Ala Pro Val Glu Ile His Gln Val Leu Asp Asn Gly Leu Leu Val
                260                 265                 270
Asp Pro His Asp Gln His Ala Ile Ala Asp Ala Leu Tyr Lys Leu Leu
                275                 280                 285
Ser Glu Lys Gln Leu Trp Ser Lys Cys Arg Glu Asn Gly Leu Lys Asn
            290                 295                 300
Ile His Gln Phe Ser Trp Pro Glu His Cys Lys Asn Tyr Leu Ser Arg
305                 310                 315                 320
Ile Ser Thr Leu Gly Pro Arg His Pro Ala Phe Ala Ser Asn Glu Asp
                325                 330                 335
Arg Ile Lys Ala Pro Ile Lys Gly Arg Lys His Val Thr Val Ile Ala
                340                 345                 350
Val Asp Ser Val Ser Lys Glu Asp Leu Ile Arg Ile Val Arg Asn Ser
                355                 360                 365
Ile Glu Ala Ala Arg Lys Glu Asn Leu Ser Gly Ser Thr Gly Phe Val
            370                 375                 380
Leu Ser Thr Ser Leu Thr Ile Gly Glu Ile His Ser Leu Leu Met Ser
385                 390                 395                 400
Ala Gly Met Leu Pro Thr Gly Phe Asp Ala Phe Ile Cys Asn Ser Gly
                405                 410                 415
Ser Asp Leu Tyr Tyr Pro Ser Cys Thr Gly Asp Thr Pro Ser Asn Ser
                420                 425                 430
Arg Val Thr Phe Ala Leu Asp Arg Ser Tyr Gln Ser His Ile Glu Tyr
                435                 440                 445
His Trp Gly Gly Glu Gly Leu Arg Lys Tyr Leu Val Lys Trp Ala Ser
            450                 455                 460
Ser Val Glu Arg Arg Gly Arg Ile Glu Lys Gln Val Ile Phe Glu
465                 470                 475                 480
Asp Pro Glu His Ser Thr Tyr Cys Leu Ala Phe Lys Val Val Asn
                485                 490                 495
Pro Asn His Leu Pro Pro Leu Lys Glu Leu Gln Lys Leu Met Arg Ile
            500                 505                 510
Gln Ser Leu Arg Cys His Ala Leu Tyr Asn His Gly Ala Thr Arg Leu
            515                 520                 525
Ser Val Ile Pro Ile His Ala Ser Arg Ser Lys Ala Leu Arg Tyr Leu
            530                 535                 540
Ser Val Arg Trp Gly Ile Glu Leu Gln Asn Val Val Leu Val Gly
545                 550                 555                 560
Glu Thr Gly Asp Ser Asp Tyr Glu Glu Leu Phe Gly Gly Leu His Lys
                565                 570                 575
Thr Val Ile Leu Lys Gly Glu Phe Asn Thr Ser Ala Asn Arg Ile His
                580                 585                 590
Ser Val Arg Arg Tyr Pro Leu Gln Asp Val Val Ala Leu Asp Ser Pro
            595                 600                 605
Asn Ile Ile Gly Ile Glu Gly Tyr Gly Thr Asp Asp Met Arg Ser Ala
610                 615                 620
Leu Lys Gln Leu Asp Ile Arg Ala Gln
625                 630

<210> SEQ ID NO 27
<211> LENGTH: 1738
<212> TYPE: DNA
<213> ORGANISM: Triticum aestivum
```

-continued

```
<400> SEQUENCE: 27
gcacgagccg ctgcttatgg tctgcccgtg gtggcaacca agaacggcgg gccggtggac      60
atcctcaagg cgcttcacaa cggcctgctg gtggacccgc actccgccga ggcgatcacc     120
ggcgcgctgc tcagcctgct ggccgacaag gggcagtggc tggagagccg acgcaacggc     180
ctgcgcaaca tccaccgctt ctcgtggccg caccactgcc gcctctacct ctcccacgtc     240
gccgcctact gcgaccaccc gtcgccgcac cagcggctcc gcgtccctgg cgtcccgtct     300
gcctcggcga gcatgggcgg tgacgactcc ctctcggact cactccgtgg cctctcgctc     360
caaatctccg tggacgcctc aacgacctc aatgccgggg actcggccgc gctgatcatg     420
gacgccctac gccgccgccc ggcggccgac aggcgcgagg gctccggcag ggcgttgggc     480
ttcgcgccgg gaaggaggca gaggctcctt gtcgtcgccg tcgactgcta cggcgatgac     540
ggcaagcccg acgtcgagca actgaagaaa gccatcgacg cggcgatgtc cgccagtgac     600
ggcgcgggag ggcggcaggg gtacgtgctc tcgaccggca tgaccatccc cgagaccgcg     660
gagacgctca aggcctgcgg cgccgacccg gccggcttcg acgcgctcat ttgcagcagc     720
ggcgcggaga tatgctaccc gtggaaggag ctgacggccg acgaggagta ctccggccac     780
gtggcgttcc ggtggcccgg cgaccacgtg aaaaccgtcg tgccgaggct cgggaaggcc     840
gacgacgcgc aggcgtccga cctcgccgtc gacgtgtccg ctggctccgt gcactgccac     900
gcctacgccg ccaccgacgc gtccaaggtg aagaaggtgg attcgatcag gcaggcgctg     960
cggatgcgcg ggttccggtg caacctcgtc tacacgcgcg cgtgcacgcg cctcaacgtc    1020
atccctctct ccgcttcccg cccacgcgcg ttgaggtacc tgtcgataca gtggggcatc    1080
gatctcgcca aggtggcggt gctcgtcggc gagaccggag acaccgaccg cgagaagctc    1140
ctgccggggc tgcacaagac ggtgatcctg ccggggatgg tctcccgcgg cagcgagcag    1200
ctcgtccgcg gcgaggacgg gtacgccacg caggacgtcg tggccatgga ctccccgaac    1260
atcatcacga tcgccgaagg ccaggctgtc tctgaccttc tcaatgccat gtgatgtgac    1320
tatgcgagag accatcctct gccccattgt ccacagctcc tacgtaattc tggcctgtaa    1380
ttttggcagg aacaggactg cagaattttc atacaaggta tacaattta tggatgtgca     1440 agcatgagca acatgtggc taataatttt ttatgtctta gcatgcctcc cagaggtctg     1500
ttgtacatat atatacactt tataaatgaa cgcaagaaag aaattgcatg tgaaaatgat    1560 gctttttta tggaattta ctcggatatg atacgagaca agtctgtgaa aaaaaaaaa      1620 aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaa      1738

<210> SEQ ID NO 28
<211> LENGTH: 437
<212> TYPE: PRT
<213> ORGANISM: Triticum aestivum

<400> SEQUENCE: 28

Ala Arg Ala Ala Ala Tyr Gly Leu Pro Val Val Ala Thr Lys Asn Gly
  1               5                  10                  15

Gly Pro Val Asp Ile Leu Lys Ala Leu His Asn Gly Leu Leu Val Asp
                 20                  25                  30

Pro His Ser Ala Glu Ala Ile Thr Gly Ala Leu Leu Ser Leu Leu Ala
             35                  40                  45

Asp Lys Gly Gln Trp Leu Glu Ser Arg Arg Asn Gly Leu Arg Asn Ile
```

```
                50                    55                    60
His Arg Phe Ser Trp Pro His His Cys Arg Leu Tyr Leu Ser His Val
 65                  70                  75                  80

Ala Ala Tyr Cys Asp His Pro Ser Pro His Gln Arg Leu Arg Val Pro
                 85                  90                  95

Gly Val Pro Ser Ala Ser Ala Ser Met Gly Gly Asp Ser Leu Ser
                100                 105                 110

Asp Ser Leu Arg Gly Leu Ser Leu Gln Ile Ser Val Asp Ala Ser Asn
                115                 120                 125

Asp Leu Asn Ala Gly Asp Ser Ala Ala Leu Ile Met Asp Ala Leu Arg
130                 135                 140

Arg Arg Pro Ala Ala Asp Arg Arg Glu Gly Ser Gly Arg Ala Leu Gly
145                 150                 155                 160

Phe Ala Pro Gly Arg Arg Gln Arg Leu Leu Val Val Ala Val Asp Cys
                165                 170                 175

Tyr Gly Asp Asp Gly Lys Pro Asp Val Glu Gln Leu Lys Lys Ala Ile
                180                 185                 190

Asp Ala Ala Met Ser Ala Ser Asp Gly Ala Gly Gly Arg Gln Gly Tyr
                195                 200                 205

Val Leu Ser Thr Gly Met Thr Ile Pro Glu Thr Ala Glu Thr Leu Lys
                210                 215                 220

Ala Cys Gly Ala Asp Pro Ala Gly Phe Asp Ala Leu Ile Cys Ser Ser
225                 230                 235                 240

Gly Ala Glu Ile Cys Tyr Pro Trp Lys Glu Leu Thr Ala Asp Glu Glu
                245                 250                 255

Tyr Ser Gly His Val Ala Phe Arg Trp Pro Gly Asp His Val Lys Thr
                260                 265                 270

Val Val Pro Arg Leu Gly Lys Ala Asp Asp Ala Gln Ala Ser Asp Leu
                275                 280                 285

Ala Val Asp Val Ser Ala Gly Ser Val His Cys His Ala Tyr Ala Ala
                290                 295                 300

Thr Asp Ala Ser Lys Val Lys Lys Val Asp Ser Ile Arg Gln Ala Leu
305                 310                 315                 320

Arg Met Arg Gly Phe Arg Cys Asn Leu Val Tyr Thr Arg Ala Cys Thr
                325                 330                 335

Arg Leu Asn Val Ile Pro Leu Ser Ala Ser Arg Pro Arg Ala Leu Arg
                340                 345                 350

Tyr Leu Ser Ile Gln Trp Gly Ile Asp Leu Ala Lys Val Ala Val Leu
                355                 360                 365

Val Gly Glu Thr Gly Asp Thr Asp Arg Glu Lys Leu Leu Pro Gly Leu
                370                 375                 380

His Lys Thr Val Ile Leu Pro Gly Met Val Ser Arg Gly Ser Glu Gln
385                 390                 395                 400

Leu Val Arg Gly Glu Asp Gly Tyr Ala Thr Gln Asp Val Val Ala Met
                405                 410                 415

Asp Ser Pro Asn Ile Ile Thr Ile Ala Glu Gly Gln Ala Val Ser Asp
                420                 425                 430

Leu Leu Asn Ala Met
                435

<210> SEQ ID NO 29
<211> LENGTH: 1057
<212> TYPE: PRT
<213> ORGANISM: Citrus unshiu
```

<400> SEQUENCE: 29

| | | | | | | | | | | | | | | |
|---|---|---|---|---|---|---|---|---|---|---|---|---|---|---|
|Met|Ala|Gly|Asn|Asp|Trp|Ile|Asn|Ser|Tyr|Leu|Glu|Ala|Ile|Leu|Asp|
|1| | | |5| | | | |10| | | | |15| |
|Val|Gly|Pro|Gly|Leu|Asp|Asp|Ala|Lys|Ser|Ser|Leu|Leu|Leu|Arg|Glu|
| | | |20| | | | |25| | | | |30| | |
|Arg|Gly|Arg|Phe|Ser|Pro|Thr|Arg|Tyr|Phe|Val|Glu|Glu|Val|Ile|Thr|
| | |35| | | | |40| | | | |45| | | |
|Gly|Phe|Asp|Glu|Thr|Asp|Leu|His|Arg|Ser|Trp|Val|Lys|Ala|Gln|Ala|
| |50| | | | |55| | | | |60| | | | |
|Thr|Arg|Ser|Pro|Gln|Glu|Arg|Asn|Thr|Arg|Leu|Glu|Asn|Met|Cys|Trp|
|65| | | | |70| | | | |75| | | | |80|
|Arg|Ile|Trp|Asn|Leu|Ala|Arg|Gln|Lys|Lys|Gln|Leu|Glu|Gly|Glu|Ala|
| | | | |85| | | | |90| | | | |95| |
|Ala|Gln|Arg|Met|Ala|Lys|Arg|Leu|Glu|Arg|Glu|Arg|Gly|Arg|Arg|
| | | |100| | | | |105| | | | |110| | |
|Glu|Ala|Thr|Ala|Asp|Met|Ser|Glu|Asp|Leu|Ser|Glu|Gly|Glu|Lys|Gly|
| | |115| | | | |120| | | | |125| | | |
|Asp|Ile|Val|Ser|Asp|Val|Ser|Ala|His|Gly|Asp|Ser|Thr|Arg|Ser|Arg|
| |130| | | | |135| | | | |140| | | | |
|Leu|Pro|Arg|Ile|Ser|Ser|Val|Asp|Ala|Met|Glu|Thr|Trp|Ile|Ser|Gln|
|145| | | | |150| | | | |155| | | | |160|
|Gln|Lys|Gly|Lys|Lys|Leu|Tyr|Ile|Val|Leu|Ile|Ser|Ile|His|Gly|Leu|
| | | | |165| | | | |170| | | | |175| |
|Ile|Arg|Gly|Glu|Asn|Met|Glu|Leu|Gly|Arg|Asp|Ser|Asp|Thr|Gly|Gly|
| | | |180| | | | |185| | | | |190| | |
|Gln|Val|Lys|Tyr|Val|Val|Glu|Leu|Ala|Arg|Ala|Leu|Gly|Ser|Met|Pro|
| | |195| | | | |200| | | | |205| | | |
|Gly|Val|Tyr|Arg|Val|Asp|Leu|Leu|Thr|Arg|Gln|Val|Ser|Ala|Pro|Asp|
| |210| | | | |215| | | | |220| | | | |
|Val|Asp|Trp|Ser|Tyr|Gly|Glu|Pro|Thr|Glu|Met|Leu|Thr|Pro|Arg|Asn|
|225| | | | |230| | | | |235| | | | |240|
|Ser|Asp|Asp|Phe|Met|Asp|Met|Gly|Glu|Ser|Ser|Gly|Ala|Tyr|Ile|
| | | | |245| | | | |250| | | | |255| |
|Ile|Arg|Ile|Pro|Phe|Gly|Pro|Lys|Asp|Lys|Tyr|Ile|Ala|Lys|Glu|Leu|
| | | |260| | | | |265| | | | |270| | |
|Leu|Trp|Pro|His|Ile|Pro|Glu|Phe|Val|Asp|Gly|Ala|Leu|Asn|His|Ile|
| | |275| | | | |280| | | | |285| | | |
|Ile|Arg|Met|Ser|Asn|Val|Leu|Gly|Glu|Gln|Ile|Gly|Gly|Lys|Pro|
| |290| | | | |295| | | | |300| | | | |
|Val|Trp|Pro|Val|Ala|Ile|His|Gly|His|Tyr|Ala|Asp|Ala|Gly|Asp|Ser|
|305| | | | |310| | | | |315| | | | |320|
|Ala|Ala|Leu|Leu|Ser|Gly|Ala|Leu|Asn|Val|Pro|Met|Leu|Phe|Thr|Gly|
| | | | |325| | | | |330| | | | |335| |
|His|Ser|Leu|Gly|Arg|Asp|Lys|Leu|Glu|Gln|Leu|Leu|Lys|Gln|Ala|Arg|
| | | |340| | | | |345| | | | |350| | |
|Leu|Ser|Arg|Asp|Glu|Ile|Asn|Ala|Thr|Tyr|Lys|Ile|Met|Arg|Arg|Ile|
| | |355| | | | |360| | | | |365| | | |
|Glu|Ala|Glu|Glu|Leu|Ser|Leu|Asp|Ala|Ser|Glu|Ile|Val|Ile|Thr|Ser|
| |370| | | | |375| | | | |380| | | | |
|Thr|Arg|Gln|Glu|Ile|Glu|Glu|Gln|Trp|Arg|Leu|Tyr|Asp|Gly|Phe|Asp|
|385| | | | |390| | | | |395| | | | |400|
|Pro|Val|Leu|Glu|Arg|Lys|Leu|Arg|Ala|Arg|Ile|Lys|Arg|Asn|Val|Ser|

-continued

```
                405                 410                 415
Cys Tyr Gly Lys Phe Met Pro Arg Met Ala Ile Ile Pro Pro Gly Met
            420                 425                 430
Glu Phe His His Ile Val Pro Gln Asp Gly Met Asp Gly Glu Thr
        435                 440                 445
Glu Gly Asn Glu Asp Asn Pro Ala Ser Pro Asp Pro Ile Trp Ser
    450                 455                 460
Glu Ile Met Arg Phe Phe Thr Asn Pro Arg Lys Pro Val Ile Leu Ala
465                 470                 475                 480
Leu Ala Arg Pro Asp Pro Lys Lys Asn Ile Thr Thr Leu Val Lys Ala
                485                 490                 495
Phe Gly Glu Cys Arg Pro Leu Arg Glu Leu Ala Asn Leu Thr Leu Ile
            500                 505                 510
Met Gly Asn Arg Asp Gly Ile Asp Glu Met Ser Ser Thr Ser Ala Ser
            515                 520                 525
Val Leu Leu Ser Val Leu Lys Leu Ile Asp Lys Tyr Asp Leu Tyr Gly
        530                 535                 540
Gln Val Ala Tyr Pro Lys His His Lys Gln Ser Asp Val Pro Glu Ile
545                 550                 555                 560
Tyr Arg Leu Ala Ala Lys Thr Lys Gly Val Phe Ile Asn Pro Ala Phe
                565                 570                 575
Ile Glu Pro Phe Gly Leu Thr Leu Ile Glu Ala Ala His Gly Leu
            580                 585                 590
Pro Ile Val Ala Thr Lys Asn Gly Gly Pro Val Asp Ile His Arg Val
            595                 600                 605
Leu Asp Asn Gly Leu Leu Val Asp Pro His Asp Gln Gln Ser Ile Ala
        610                 615                 620
Asp Ala Leu Leu Lys Leu Val Ala Gly Lys Gln Leu Trp Ala Arg Cys
625                 630                 635                 640
Arg Gln Asn Gly Leu Lys Asn Ile His Leu Phe Ser Trp Pro Glu His
                645                 650                 655
Cys Lys Thr Tyr Leu Ser Arg Ile Ala Gly Cys Lys Pro Arg His Pro
            660                 665                 670
Gln Trp Gln Arg Thr Asp Asp Gly Gly Glu Thr Ser Glu Ser Asp Ser
            675                 680                 685
Pro Gly Asp Ser Leu Arg Asp Ile Gln Asp Ile Ser Leu Asn Leu Lys
        690                 695                 700
Phe Ser Leu Asp Gly Glu Lys Ser Gly Ala Ser Gly Asn Asp Asp Ser
705                 710                 715                 720
Leu Asp Ser Glu Gly Asn Val Ala Asp Arg Lys Ser Arg Leu Glu Asn
                725                 730                 735
Ala Val Leu Ala Trp Ser Lys Gly Val Leu Lys Asp Thr Arg Lys Ser
            740                 745                 750
Gly Ser Thr Asp Lys Val Asp Gln Asn Thr Gly Ala Ala Lys Phe Pro
        755                 760                 765
Ala Leu Arg Arg Arg Lys His Ile Phe Val Ile Ser Val Asp Cys Asp
    770                 775                 780
Ser Thr Thr Gly Leu Leu Asp Ala Thr Lys Lys Ile Cys Glu Ala Val
785                 790                 795                 800
Glu Lys Glu Arg Thr Glu Gly Ser Ile Gly Phe Ile Leu Ser Thr Ser
                805                 810                 815
Met Thr Ile Ser Glu Ile His Ser Phe Leu Val Ser Gly His Leu Ser
            820                 825                 830
```

```
Pro Ser Asp Phe Asp Ala Phe Ile Cys Asn Ser Gly Ser Asp Leu Tyr
        835             840             845

Tyr Ser Thr Leu Asn Ser Glu Asp Gly Pro Phe Val Val Asp Phe Tyr
    850             855             860

Tyr His Ser His Ile Glu Tyr Arg Trp Gly Gly Glu Gly Leu Arg Lys
865             870             875             880

Thr Leu Val Arg Trp Ala Ser Gln Val Thr Asp Lys Lys Ala Glu Ser
            885             890             895

Gly Glu Lys Val Leu Thr Pro Ala Glu Gln Leu Ser Thr Asn Tyr Cys
            900             905             910

Tyr Ala Phe Ser Val Gln Lys Pro Gly Met Thr Pro Pro Val Lys Glu
        915             920             925

Leu Arg Lys Val Leu Arg Ile Gln Ala Leu Arg Cys His Val Ile Tyr
    930             935             940

Cys Gln Asn Gly Ser Arg Val Asn Val Ile Pro Val Leu Ala Ser Arg
945             950             955             960

Ser Gln Ala Leu Arg Tyr Leu Tyr Leu Arg Trp Gly Val Glu Leu Ser
            965             970             975

Lys Met Val Val Phe Val Gly Glu Ser Gly Asp Thr Asp Tyr Glu Gly
            980             985             990

Leu Leu Gly Gly Val His Lys Thr Val Ile Leu Lys Gly Ile Cys Ser
        995             1000            1005

Ser Ser Ser Asn Gln Ile His Ala Asn Arg Ser Tyr Pro Leu Ser Asp
    1010            1015            1020

Val Met Pro Ile Asp Ser Pro Asn Ile Val Gln Thr Pro Glu Asp Cys
1025            1030            1035            1040

Thr Thr Ser Asp Ile Arg Ser Ser Leu Glu Gln Leu Gly Leu Leu Lys
            1045            1050            1055

Val
```